(12) United States Patent
Wiig et al.

(10) Patent No.: US 8,691,962 B2
(45) Date of Patent: Apr. 8, 2014

(54) PEROXIDASE GENE NEMATODE INDUCIBLE PROMOTORS AND METHODS OF USE

(75) Inventors: Aaron Wiig, Chapel Hill, NC (US); Robert Ascenzi, Cary, NC (US); Xiang Huang, Apex, NC (US); Sumita Chaudhuri, Cary, NC (US); Rui-Guang Zhen, Chapel Hill, NC (US); Yu Han, Cary, NC (US)

(73) Assignee: BASF Plant Science GmbH (DE)

( * ) Notice: Subject to any disclaimer, the term of this patent is extended or adjusted under 35 U.S.C. 154(b) by 1011 days.

(21) Appl. No.: 12/519,530

(22) PCT Filed: Dec. 20, 2007

(86) PCT No.: PCT/EP2007/064356
§ 371 (c)(1),
(2), (4) Date: Jun. 17, 2009

(87) PCT Pub. No.: WO2008/077892
PCT Pub. Date: Jul. 3, 2008

(65) Prior Publication Data
US 2010/0077506 A1    Mar. 25, 2010

Related U.S. Application Data

(60) Provisional application No. 60/876,416, filed on Dec. 22, 2006.

(51) Int. Cl.
*C12N 15/63* (2006.01)
*C12N 15/82* (2006.01)
*A01H 5/00* (2006.01)

(52) U.S. Cl.
USPC .......... 536/24.1; 800/287; 435/320.1

(58) Field of Classification Search
None
See application file for complete search history.

(56) References Cited

U.S. PATENT DOCUMENTS

2001/0047525 A1*  11/2001  Bruce et al. ............. 800/298

FOREIGN PATENT DOCUMENTS

| WO | WO 01/38485    | 5/2001 |
| WO | WO 2005/080557 | 9/2005 |
| WO | WO 2006/032707 | 3/2006 |
| WO | WO 2006/102343 | 9/2006 |

OTHER PUBLICATIONS

Kaneko et al. 1998, Genbank accession:AB010692.*
Liu et al. 1999, PNAS 96:6535-6540.*
Mitra Mazarei, et al, "Homologous soybean and Arabidopsis genes share responsiveness to cyst nematode infection" Molecular Plant Pathology, 2004 5(5) 409-423, Blackwell Publis.

* cited by examiner

*Primary Examiner* — Li Zheng
(74) *Attorney, Agent, or Firm* — Patricia A. McDaniels

(57) ABSTRACT

The invention provides isolated plant gene promoters and regulatory elements that are root specific and/or induced by plant parasitic nematodes. The promoters of the invention are useful for controlling expression of nucleic acids of interest in plant roots and are particularly useful for controlling transcription of nucleic acids encoding agents that disrupt formation or maintenance of parasitic nematode feeding sites in plants.

10 Claims, 9 Drawing Sheets

Figure 1

```
   1   CGAAGAGCAT AAGTTTTGTT CAAATGGCCC AATAACAAAT TAAAAACATG
  51   TAAAGTAGTC AGTTTAAACA AGCATTTGCA TAAAGTGTGG TTAATATTAT
 101   ATTAAACTTC ACATCCAATG AGCATTCATG TAATTTAAAG TAACTGAAGT
 151   TAAGTATCTA GAAGCCTTTT TCTTCTATTG GTTATTAATT TGCTTAATTT
 201   TCTTTATAAG TTAATTTCTG GTTGGTGTGA AAATGTGACC GGAGAAGGTA
 251   TCTAACTTTT TTTTTTCTTT AATGAATTCC ACTAAAATTT AATTCTGTAT
 301   GTAACGCATA TAGTAAAATC TAGAAAGCGA CCGGCGTGCC TCCTTTGGAA
 351   AGTAATCCTG TAAAAGTAAA AGCCGCGTAG TGTAAAAGTA TATGACTTCT
 401   TCTTCCCATA ATTATTTTAT AATTAGTCTT TAATCTAAAT ATTTAAACAT
 451   ATAATTCGTT TTACGAGAAA GATCTTCACA CTCGATTAGT ATACATTACA
 501   TTTAATTCCC TAGTTCATAA AATGGATAAC AAAAGGCTGT GCGAGATTAC
 551   AACTGTACTT GATAATTTTG TATAAATATA TCCTTTATGA ATATATTTTA
 601   GCATTGATGA CCGTACATGG TTAATCCAGT CTGCAGCATA ACGGAGTATG
 651   ATATTAAATG AACACTTTCT GTTCGTATCA ATGGTATCG AATATTATTA
 701   GAGTGATCAT TCAGAAGAAA AAAAGAGAGA GAAGAAAACC TACAGTGTAA
 751   ACATTTTTTT TTTTGCTAAA TACCTACAGT GTAAACATGA AGTGCTATAA
 801   TTTCTGCAAA TAGAAATCAA GAACAGAAAG AGTTGCTTGG AGGAAAAGAA
 851   ATAGAAAATT AAGAAATCTA GTGATGTAAT AAATCTTTCC ATAAAATCAA
 901   ATGTTTGGTC CAAAGTATTA GTTAAATAAT TAGGCCACTA TTCTTGACAA
 951   CTCTTTTTAA CAAACTCTTC TATATTTCT CGTGGTACAT ATGCTGAAAA
1001   AGATGTATGT CTAATCCATA ATATATCTGT ATAATGCGAC TTTCATTATC
1051   TATTAGTACG ACTTCTAACC TAGAAGATAA CAAGCATTAG CTAGGGCATC
1101   AAAATCAACG TGGAAAAACC TACGAAAAGC ACGAAGTGAT TAATCTGTGT
1151   AGGGGTGGCG TAAGGGTAAA GACTAAAGAC TGAGAATCTA GGGTTCAAGG
1201   CGTAAACTTG TTCTGCTTTT TGGGTTTCAT TTTATTGGCG AACAACATTG
1251   ATGTGTGTGG ACCATTTGGT GTTCAGGGAT TGAGACAAGA TAATATGTTT
1301   GCTCTCACCT TCTAGGATTA CTCGGGTGCT AAGACTCACT TAGTACTATT
1351   GCTATATCGA TATACTAGTT CATTACCAAA AAATGGAGTC TTCAAATTTC
1401   GAGTTCCAAT ATCTGAAAGC ATTGTTTAAA GAGATTTGTT TTCTCCCTGC
1451   ACAATTAGTT TATAACTTCA TATATACACA ATCTTATCAA TTTACAACCA
1501   GGTGTGTGTG AACCTTCACA TAATCTCTCT TATTCATTCA TGTATATATC
1551   CAATAAAAGT TCGATATGTG AAATTATATA TCTCCATCTA ATGTTAGACT
1601   ATTCCCGGGT CTTGACTATA AATTTAAAGT ATTAGACGAG CTAATTATAT
1651   TTAGCACAAA CAATTTCTTC TGTAACAGTG TCACGCTTAT CACTACCAAA
1701   GAATAAACAC TGATCTGTTT TAATCTCTTA TTTTCTCACC CATATTCAAA
1751   GTCAACTATT GCAAGACTTC GAGATAATTA ATTTGATGGC TATACTATTT
1801   ACTTGACATT TGGGAAAATA TATTTTCGCT GATAAATTTG GTTTTTACTT
1851   CTCTCTCCGA CGGATATAGA AACAATTCAA TTACATGCGA AATGATAAT
1901   TCAACCCTAT AAACCAAAAC AAATAACAGA ATGCACATTT TTTTCAACGC
1951   GTTAGGTCAC CTATCTTTCA CTTTAGAACA TCCCTTCACG TCTCTATATA
2001   AACCTCGACT CTGTTATCCT TTGTTCTTCA AGTACAACAA TCAACTCTAA
2051   GTCTATTATA TTCAAGTCTT TGTTTTAACC TAACA     (SEQ ID NO:1)
```

Figure 2

```
   1    AGCAAACACA AACACTTGAA GTACTAAGTT AGTGTTTTTG AGCAAACTAT
  51    GGCTTCGTTT TGTTCTAGAT TGACCATTTG TTTGGCTCTG TTTGTCCTCA
 101    TATTGGGGAG TGCCAATGCC CAACTTTCTA CAAACTTCTA CTACCATTCG
 151    TGTCCAAACC TCTTCTCCAC TGTGAAATCC ACAGTGCAAT CTGCCATATC
 201    AAAGGAGACC CGCATGGGTG CTTCTCTCCT CCGCCTGTTC TTCCACGATT
 251    GCTTTGTCAA TGGATGTGAT GGTTCAATTC TATTGGATGA CACATCAAGC
 301    TTCACCGGAG AGAAGAACGC AAACCCCAAC AGGAACTCTG CTCGTGGATA
 351    CGAGGTCATT GACAACATTA AATCAGCCGT GGAGAAAGCA TGTCCAGGAG
 401    TTGTCTCCTG CGCAGATATC CTTGCCATAG CTGCCAGAGA CTCTGTTCAG
 451    ATCCTTGGAG GCCCTAGTTG GAATGTTAAA GTTGGAAGAA GAGACGCTAG
 501    AACTGCTAGC CAATCTGCTG CTAACAATGG CATCCCTCCA CCCACTTCAA
 551    ACCTTAACCA ACTCATCTCA AGATTCAGCG CTCTTGGACT TTCCACCAAG
 601    GACTTGGTCG CCTTGTCCGG TGGTCACACA ATTGGACAAG CAAGGTGCAC
 651    AAACTTCAGA GCCCGCATCT ACAACGAGAG CAACATAGAC ACCGCATTTG
 701    CAAGGACAAG GCAACAAAGC TGCCCAAGAA CATCAGGGTC AGGGGACAAT
 751    AATCTTGCAA CGCTTGATCT TCAAACTCCA ACCGAATTCG ACAACTACTA
 801    CTTCAAGAAT CTTGTTCAGA AGAAGGGTCT CCTCCACTCT GATCAGCAAC
 851    TGTTCAATGG TGGGTCCACC GACTCCATTG TGCGTGGCTA CAGCACCAAC
 901    CCGAGCTCCT TCTCCTCTGA CTTCGCCGCC GCCATGATCA AGATGGGAGA
 951    CATTAGTCCT CTCACTGGCT CCAACGGAGA AATCAGGAAG AATTGTAGAA
1001    GGATTAACTA ATTACTAATT GAGTCTCCAA TATTAAGGGT CCTACTACAC
1051    ATACGCAAGC AATTTAATTG TGTTTAATAA GTTGTTAAAA CATGTTTTGG
1101    TTGTGTTTTG GATTCCGTGG TGGGTTAATT TCCTAGTGTA GTTGCTGTTA
1151    TCAATGCCGT ATACGTTAGT GTGTGTTCTA CTTCCCTTTA TTTTTGTCTC
1201    TTTTTTACTT TTCCTTGACT ATATTGTAGG AAAAAAAATC CTTTATCAAG
1251    AATTTATCAA GAACAGAGTT TGCTTTTTTG AGACCGACAC GCAGCGGCCG
1301    C
```
(SEQ ID NO:2)

Figure 3

```
  1    MASFCSRLTI  CLALFVLILG  SANAQLSTNF  YYHSCPNLFS  TVKSTVQSAI
 51    SKETRMGASL  LRLFFHDCFV  NGCDGSILLD  DTSSFTGEKN  ANPNRNSARG
101    YEVIDNIKSA  VEKACPGVVS  CADILAIAAR  DSVQILGGPS  WNVKVGRRDA
151    RTASQSAANN  GIPPPTSNLN  QLISRFSALG  LSTKDLVALS  GGHTIGQARC
201    TNFRARIYNE  SNIDTAFART  RQQSCPRTSG  SGDNNLATLD  LQTPTEFDNY
251    YFKNLVQKKG  LLHSDQQLFN  GGSTDSIVRG  YSTNPSSFSS  DFAAAMIKMG
301    DISPLTGSNG  EIRKNCRRIN  *  (SEQ ID NO:3)
```

Figure 4

| Gene Name | Syncytia #1(N)¶ | Syncytia #2 (N) | Non-Syncytia | Control Roots |
|---|---|---|---|---|
| 59712764 | 1593±314 (4) | 799±127 (5) | ND | ND |

Figure 5

```
  1    MASNKLISIL VLVVTLLLQG DNNYVVEAQL TTNFYSTSCP NLLSTVQTAV
 51    KSAVNSEARM GASILRLFFH DCFVNGCDGS ILLDDTSSFT GEQNAAPNRN
101    SARGFNVIDN IKSAVEKACP GVVSCADILA IAARDSVVAL GGPNWNVKVG
151    RRDARTASQA AANSNIPAPT SSLSQLISSF SAVGLSTRDM VALSGAHTIG
201    QSRCTNFRAR IYNETNINAA FATTRQRTCP RASGSGDGNL APLDVTTAAS
251    FDNNYFKNLM TQRGLLHSDQ VLFNGGSTDS IVRGYSNNPS SFNSDFTAAM
301    IKMGDISPLT GSSGEIRKVC GRTN*   (SEQ ID NO:4)
```

Figure 6

```
                      1                                                 50
SEQ ID NO:3    (1)    MASFCSRLTICLALFVLILGSAN------AQLSTNFYYHSCPNLFSTVKSTV
SEQ ID NO:4    (1)    MASNKLISILVLVVTLLLQGDNNYVVEAQLTTNFYSTSCPNLLSTVQTAV
SEQ ID NO:7    (1)    MAS     I L LLI G  N     AQLSTNFY  SCPNL STV S V 51                                                100
SEQ ID NO:3    (47)   QSAISKETRMGASLLRLFFHDCFVNGCDGSILLDDTSSFTGEKNANPNRN
SEQ ID NO:4    (51)   KSAVNSEARMGASILRLFFHDCFVNGCDGSILLDDTSSFTGEQNAAPNRN
SEQ ID NO:7    (51)    SAI  E RMGASILRLFFHDCFVNGCDGSILLDDTSSFTGE NA PNRN 101                                               150
SEQ ID NO:3    (97)   SARGYEVIDNIKSAVEKACPGVVSCADILAIAARDSVQILGGPSWNVKVG
SEQ ID NO:4    (101)  SARGFNVIDNIKSAVEKACPGVVSCADILAIAARDSVVALGGPNWNVKVG
SEQ ID NO:7    (101)  SARGF VIDNIKSAVEKACPGVVSCADILAIAARDSV  LGGP WNVKVG 151                                               200
SEQ ID NO:3    (147)  RRDARTASQSAANNGIPPPTSNLNQLISRFSALGLSTKDLVALSGGHTIG
SEQ ID NO:4    (151)  RRDARTASQAAANSNIPAPTSSLSQLISSFSAVGLSTRDMVALSGAHTIG
SEQ ID NO:7    (151)  RRDARTASQAAAN  IP PTS L QLIS FSALGLSTKDLVALSGAHTIG 201                                               250
SEQ ID NO:3    (197)  QARCTNFRARIYNESNIDTAFARTRQQSCPRTSGSGDNNLATLDLQTPTE
SEQ ID NO:4    (201)  QSRCTNFRARIYNETNINAAFATTRQRTCPRASGSGDGNLAPLDVTTAAS
SEQ ID NO:7    (201)  QARCTNFRARIYNESNI  AFA TRQ  SCPR SGSGD NLA LDL T 251                                               300
SEQ ID NO:3    (247)  FDNYYFKNLVQKKGLLHSDQQLFNGGSTDSIVRGYSTNPSSFSSDFAAAM
SEQ ID NO:4    (251)  FDNNYFKNLMTQRGLLHSDQVLFNGGSTDSIVRGYSNNPSSFNSDFTAAM
SEQ ID NO:7    (251)  FDN YFKNLM   KGLLHSDQ LFNGGSTDSIVRGYS NPSSF SDF AAM 301            324
SEQ ID NO:3    (297)  IKMGDISPLTGSNGEIRKNCRRIN
SEQ ID NO:4    (301)  IKMGDISPLTGSSGEIRKVCGRTN
SEQ ID NO:7    (301)  IKMGDISPLTGS GEIRK C R N
```

Figure 7

Nematode infected:

| SeqID | Construct | Root tip | Vascular | Cortical | Syncytia |
|---|---|---|---|---|---|
| 1 | pAW283 | - | - | - | + |

Control uninfected:

| SeqID | Construct | Root tip | Vascular | Cortical |
|---|---|---|---|---|
| 1 | pAW283 | - | - | - |

Figure 8

Nematode infected:

| SeqID | Construct | Root tip | Vascular | Cortical | Syncytia |
|---|---|---|---|---|---|
| 1 | pAW283 | - | - | - | + |
| 1 (bases 631-2085) | RAW448 | - | - | - | - |
| 1 (bases 1604-2085) | RAW437 | - | + | - | + |

Control uninfected:

| SeqID | Construct | Root tip | Vascular | Cortical |
|---|---|---|---|---|
| 1 | pAW283 | - | - | - |
| 1 (bases 631-2085) | RAW448 | - | - | - |
| 1 (bases 1604-2085) | RAW437 | - | + | - |

Figure 9

Common Primers

At5g05340For (SEQ ID NO:5)
5' CCCGGGCGAAGAGCATAAGTTTTGTTC 3'

At5g05340Rev (SEQ ID NO:6)
5' GGCGCGCCTGTTAGGTTAAAACAAAGACTTG 3'

PEROXIDASE GENE NEMATODE INDUCIBLE PROMOTORS AND METHODS OF USE

This application is a national stage application under 35 U.S.C. §371 of PCT/EP2007/064356, filed Dec. 20, 2007, which claims benefit of U.S. provisional application No. 60/876,416, filed Dec. 22, 2006. The entire contents of each of the above-identified applications are incorporated herein by reference.

FIELD OF THE INVENTION

This invention relates to promoters and regulatory elements that regulate transcription of genes similar to that of the *Arabidopsis thaliana* peroxidase (POX) gene having identifier At5g05340. The promoters of the present invention are useful for controlling transcription of any nucleic acid of interest in plant roots. In particular, the promoters of the invention may be used to control transcription of nucleic acids encoding agents that disrupt the formation or maintenance of the feeding site, disrupt the growth and/or reproduction of plant parasitic nematodes, that confer or improve plant resistance to plant parasitic nematodes, or that are toxic to plant parasitic nematodes to reduce crop destruction.

BACKGROUND OF THE INVENTION

Nematodes are microscopic roundworms that feed on the roots, leaves and stems of more than 2,000 row crops, vegetables, fruits, and ornamental plants, causing an estimated $100 billion crop loss worldwide. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore pathogenic on a large number of crop species. The cyst- and lesion-forming nematode species have a more limited host range, but still cause considerable losses in susceptible crops.

Pathogenic nematodes are present throughout the United States, with the greatest concentrations occurring in the warm, humid regions of the South and West and in sandy soils. Soybean cyst nematode (*Heterodera glycines*), the most serious pest of soybean plants, was first discovered in the United States in North Carolina in 1954. Some areas are so heavily infested by soybean cyst nematode (SCN) that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematode infestation can cause significant yield losses without any obvious above-ground disease symptoms. The primary causes of yield reduction are due to root damage underground. Roots infected by SCN are dwarfed or stunted. Nematode infestation also can decrease the number of nitrogen-fixing nodules on the roots, and may make the roots more susceptible to attacks by other soil-borne plant pathogens.

The nematode life cycle has three major stages: egg, juvenile, and adult. The life cycle varies between species of nematodes. For example, the SCN life cycle can usually be completed in 24 to 30 days under optimum conditions whereas other species can take as long as a year, or longer, to complete the life cycle. When temperature and moisture levels become favorable in the spring, worm-shaped juveniles hatch from eggs in the soil. Only nematodes in the juvenile developmental stage are capable of infecting soybean roots.

The life cycle of SCN has been the subject of many studies, and as such are a useful example for understanding the nematode life cycle. After penetrating soybean roots, SCN juveniles move through the root until they contact vascular tissue, at which time they stop migrating and begin to feed. With a stylet, the nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As female nematodes feed, they swell and eventually become so large that their bodies break through the root tissue and are exposed on the surface of the root.

After a period of feeding, male SCN nematodes, which are not swollen as adults, migrate out of the root into the soil and fertilize the enlarged adult females. The males then die, while the females remain attached to the root system and continue to feed. The eggs in the swollen females begin developing, initially in a mass or egg sac outside the body, and then later within the nematode body cavity. Eventually the entire adult female body cavity is filled with eggs, and the nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the protective cysts for several years.

A nematode can move through the soil only a few inches per year on its own power. However, nematode infestation can be spread substantial distances in a variety of ways. Anything that can move infested soil is capable of spreading the infestation, including farm machinery, vehicles and tools, wind, water, animals, and farm workers. Seed sized particles of soil often contaminate harvested seed. Consequently, nematode infestation can be spread when contaminated seed from infested fields is planted in non-infested fields. There is even evidence that certain nematode species can be spread by birds. Only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of nematode-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. U.S. Pat. Nos. 5,589,622 and 5,824,876 disclose eight promoters isolated from potato roots infected with *Globodera rostochiensis*: no nematode-inducible promoters from other plant species are disclosed. These promoters are purported to be useful to direct the specific expression of toxic proteins or enzymes, or the expression of antisense RNA to a target gene or to general cellular genes.

U.S. Pat. No. 5,023,179 discloses a promoter enhancer element designated ASF-1, isolated from the CaMV promoter, which is purported to enhance plant gene expression in roots.

U.S. Pat. No. 5,750,386 discloses a deletion fragment of the RB7 root specific promoter of *Nicotiana tabacum*, which is purported to be nematode-responsive.

U.S. Pat. No. 5,837,876 discloses a root cortex specific gene promoter isolated from tobacco and designated TobRD2.

U.S. Pat. No. 5,866,777 discloses a two-gene approach to retarding formation of a nematode feeding structure. The first gene, barnase, is under control of a promoter that drives expression at least in the feeding structure. The second gene, barstar, is under control of a promoter that drives expression in all of the plant's cells except the feeding structure. Feeding site-specific promoters disclosed in U.S. Pat. No. 5,866,777 include truncated versions of the Δ0.3TobRB7 and rolC promoters.

U.S. Pat. No. 5,955,646 discloses chimeric regulatory regions based on promoters derived from the mannopine synthase and octopine synthase genes of *Agrobacterium tumefaciens*, which are purported to be nematode-inducible.

U.S. Pat. No. 6,005,092 discloses the *N. tabacum* endo-1, 4-β-glucanase (Ntce17) promoter.

U.S. Pat. Nos. 6,262,344 and 6,395,963 disclose promoters isolated from *Arabidopsis thaliana*, which are purported to be nematode-inducible.

U.S. Pat. No. 6,448,471 discloses a promoter from *A. thaliana*, which is specific for nematode feeding sites.

U.S. Pat. No. 6,703,541 discloses cloning and isolation of maize peroxidase P7X gene and its promoter, the promoter is purported to be nematode inducible.

U.S. Pat. No. 6,593,513 discloses transformation of plants with barnase under control of the promoter of the *A. thaliana* endo-1,4-β-glucanase gene (cell) to produce plants capable of disrupting nematode attack.

U.S. Pat. No. 6,906,241 discloses use of the Ntce17 promoter in combination with a heterologous nucleic acid that encodes a nematocidal or insecticidal protein.

U.S. Pat. No. 7,078,589 discloses cloning and isolation of the soybean Pyk20 gene and promoter, which are purported to be induced by SCN infection and to show strong activity in vascular tissues.

U.S. Patent Application Publication No. 2003/0167507 discloses the promoter of soybean isoflavone synthase I, which is purported to be root specific and inducible in vegetative tissue by parasite attack.

U.S. Patent Application Publication No. 2004/0078841 discloses promoter regions of the TUB-1, RPL16A, and ARSK1 promoters of *Arabidopsis thaliana* and the PSMT$_A$ promoter from *Pisum sativum*, all of which are purported to be root-specific.

U.S. Patent Application Publication No. 2004/0029167 discloses a promoter sequence of a class II caffeic acid O-methyltransferase gene from tobacco, which is purported to be inducible in response to mechanical or chemical injury or to aggression by a pathogenic agent.

U.S. Patent Application Publication No. 2005/0262585 discloses a promoter from soybean phosphoribosylformylglycinamidine ribonucleotide synthase and deletion fragments thereof, which are purported to be responsive to nematode infection.

WO 94/10320 discloses the Δ0.3TobRB7 promoter fragment from tobacco and its use with a variety of genes for nematode feeding cell-specific expression.

WO 03/033651 discloses synthetic nematode-regulated promoter sequences designated SCP1, UCP3, and SUP.

WO 2004/029222 and its US counterpart U.S. Patent Application Publication No. 2005/0070697 disclose regulatory regions from the soybean adenosine-5'-phosphate deaminase and inositol-5-phosphatase genes, for use in improving nematode resistance in plants.

None of the above-mentioned root- or feeding-site specific promoters are currently in use in commercial seed containing an anti-nematode transgene. Although the need for such products has long been acknowledged, no one has thus far succeeded in developing nematode-resistant plants through recombinant DNA technology. A need continues to exist for root-specific and/or nematode feeding site-specific promoters to combine with transgenes encoding agents toxic to plant parasitic nematodes.

SUMMARY OF THE INVENTION

The invention provides promoter polynucleotides suitable for use in driving expression of a second polynucleotide in plant roots which are susceptible to attack by nematodes. The promoter polynucleotides of the invention are particularly useful for making agricultural crop plants resistant to infestation by nematodes. In another embodiment, the invention provides a promoter comprising an isolated promoter nucleotide capable of mediating root-preferred or pathogen-inducible expression, selected from the group consisting of a) a polynucleotide having the sequence as set forth in SEQ ID NO:1; b) a polynucleotide comprising nucleotides 1677 to 2027 or nucleotides 1604 to 2085 of a polynucleotide having the sequence as set forth in SEQ ID NO:1; c) a polynucleotide having at least 70% sequence identity to the polynucleotide of a) or b); d) a polynucleotide hybridizing under stringent conditions to the polynucleotide of a) or b); e) a polynucleotide comprising a biologically active portion of the polynucleotide of a) or b); and f) a polynucleotide comprising a fragment of at least 50 consecutive nucleotides, or at least 100 consecutive nucleotides, or at least 200 consecutive nucleotides of a polynucleotide having the sequence as set forth in SEQ ID NO:1.

In another embodiment, the invention provides a method of down-regulating genes essential for development and maintenance of a nematode feeding site, syncytia, or giant cell, by disrupting the function of promoter nucleotides of the present invention using methods known to those of skill in the art such as antisense or RNAi sequences.

The invention also relates to expression cassettes and transgenic plants which comprise the promoter nucleotides of the invention, and to methods of controlling parasitic nematode infestations in crops, wherein the methods employ recombinant nucleic acid constructs comprising the promoter nucleotides of the invention in operative association with a nucleic acid that encodes an agent that disrupts metabolism, growth, and/or reproduction of plant parasitic nematodes, that confers or improves plant resistance to plant parasitic nematodes, or that is toxic to plant parasitic nematodes to reduce crop destruction.

BRIEF DESCRIPTION OF THE DRAWINGS

FIG. 1: Nucleic acid sequence of *Arabidopsis thaliana* POX promoter region (SEQ ID NO:1) of locus At5g05340 where the TATA box nucleotides 1995-2001 are in bold.

FIG. 2: Nucleic acid sequence of *Glycine max* cDNA clone 59712764 (SEQ ID NO:2). The ATG start codon of ORF is shown in bold. The TAA stop codon shown in underline is 5' of ATG in-frame in cDNA sequence, indicating that the cDNA sequence is full-length. The TAA stop codon of ORF is shown in bold italic.

FIG. 3: Amino acid sequence encoded by *Glycine max* cDNA clone 59712764 (SEQ ID NO:3), where "*" indicates the stop codon.

FIG. 4: Microarray data of POX-like soybean cDNA clone 59712764. The symbol "¶" denotes the number of cDNA microarray measurements. The "control root" means whole root tissue aRNA derived from uninfected root segments the same age as SCN inoculated segments. The "non-syncytia" means whole root tissue aRNA (amplified RNA) derived from SCN infected roots adjacent to the infected region. This sample should not contain SCN or feeding sites but is harvested from SCN infected roots. Relative levels of gene expression are expressed as normalized signal intensities (±standard deviation) as described in Example 1.

FIG. 5: Amino acid sequence of *Arabidopsis thaliana* POX gene encoded by At5g05340 (SEQ ID NO:4), where "*" indicates the stop codon.

FIG. 6: Alignment of amino acid sequence (SEQ ID NO: 3) encoded by soybean cDNA clone 59712764 with *Arabidopsis* At5g05340 amino acid sequence SEQ ID NO:4). The consensus sequence (SEQ ID NO: 7) is also shown.

FIG. 7: β-glucuronidase expression patterns of binary vector pAW283 in the soybean hairy root assay set forth in Example 4. Soybean cyst nematode infected hairy roots and control uninfected hairy roots were stained 12 days after SCN inoculation. The following scoring index was used: "–" for no GUS staining, "+" for weak GUS staining, and "++" for strong GUS staining.

FIG. 8: β-glucuronidase expression patterns of binary vectors pAW283, RAW448, and RAW437 in the soybean hairy root assay set forth in Example 7. Soybean cyst nematode infected hairy roots and control uninfected hairy roots were stained 12 days after SCN inoculation. The following scoring index was used: "–" for no GUS staining, "+" for weak GUS staining, and "++" for strong GUS staining.

FIG. 9: PCR primers used to obtain the promoter of SEQ ID NO:1.

DETAILED DESCRIPTION OF PREFERRED EMBODIMENTS

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5$^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor, Plainview, N.Y.; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering Principles and Methods, Vols. 1-4, Plenum Press, New York.

The promoter nucleotides of the present invention may be provided isolated and/or purified from their natural environment, in substantially pure or homogeneous form, or free or substantially free of other nucleic acids of the species of origin. An "isolated" nucleic acid as used herein is also substantially free—at the time of its isolation—of other cellular materials or culture medium when produced by recombinant techniques, or substantially free of chemical precursors when chemically synthesized. The promoter nucleotides of the invention are polynucleotides. Where used herein, the term "isolated" encompasses all of these possibilities.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "promoter" or promoter polynucleotide as used herein refers to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide of interest (e.g., proximal to the transcriptional start site of a structural gene) whose transcription into mRNA it controls, and provides a site for specific binding by RNA polymerase and other transcription factors for initiation of transcription. A "constitutive promoter" refers to a promoter that is able to express the open reading frame or the regulatory element that it controls in all or nearly all of the plant tissues during all or nearly all developmental stages of the plant. "Regulated promoter" refers to promoters that direct gene expression not constitutively, but in a temporally- and/or spatially manner, and includes both tissue-specific and inducible promoters. Different promoters may direct the expression of a gene or regulatory element in different tissues or cell types, or at different stages of development, or in response to different environmental conditions. "Tissue-specific promoter" refers to regulated promoters that are not expressed in all plant cells but only in one or more cell types in specific organs (such as roots or seeds), specific tissues (such as embryo or cotyledon), or specific cell types (such as leaf parenchyma or seed storage cells). "Inducible promoter" refers to those regulated promoters that can be turned on in one or more cell types by an external stimulus, such as a chemical, light, hormone, stress, or a pathogen.

In accordance with the invention, the promoter polynucleotides of the present invention may be placed in operative association with a second polynucleotide for root-specific and/or pathogen-inducible expression of the second polynucleotide in plants in order to vary the phenotype of that plant. Preferably the pathogens are nematodes. As used herein, the terms "in operative association," "operably linked," and "associated with" are interchangeable and mean the functional linkage of a promoter polynucleotide and a second polynucleotide on a single nucleic acid fragment in such a way that the transcription of the second polynucleotide is initiated and mediated by the promoter polynucleotide. In general, polynucleotides that are in operative association are contiguous.

Any second polynucleotide may be placed in operative association with the promoter polynucleotide of the invention to effect root-specific or pathogen-inducible expression of the second polynucleotide. Second polynucleotides include, for example, an open reading frame, a portion of an open reading frame, a polynucleotide encoding a fusion protein, an anti-sense polynucleotide, a polynucleotide encoding a double-stranded RNA construct, a transgene, and the like. The second polynucleotide may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like.

Preferably, the second polynucleotide encodes a double-stranded RNA (dsRNA) or anti-sense polynucleotide, which is substantially identical or homologous in whole or in part to a plant gene required for formation or maintenance of a nematode feeding site. The second polynucleotide may alternatively encode an agent that disrupts the growth and/or reproduction of plant parasitic nematodes, that confers or improves plant resistance to plant parasitic nematodes, or that is toxic to plant parasitic nematodes to reduce crop destruction. Any polynucleotide encoding an agent that disrupts the growth and/or reproduction of plant parasitic nematodes, that confers or improves plant resistance to plant parasitic nematodes, or that is toxic to plant parasitic nematodes may be employed in accordance with the invention. For example, the second polynucleotide may encode a double-stranded RNA that is substantially identical to a target gene of a parasitic plant nematode that is essential for metabolism, survival, metamorphosis, or reproduction of the nematode. The second polynucleotide may encode a double-stranded RNA that is substantially identical to a plant gene in the feeding sites of the plant roots that is essential for the survival of the nematode. As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene. Exemplary plant parasitic nematode target genes are set forth, for example, in commonly assigned copending U.S. Patent Application Publication No. 2005/188438, incorporated herein by reference.

Alternatively, for nematode control, the second polynucleotide placed in operative association with the promoter polynucleotides of the invention may encode a nematode-toxic protein. For example, nucleic acids encoding microbial toxins or fragments thereof, toxins or fragments thereof derived from insects such as those described in U.S. Pat. Nos. 5,457,178; 5,695,954; 5,763,568; 5,959,182; and the like, are useful in this embodiment of the invention.

Crop plants and corresponding pathogenic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes that are targeted by the present invention include, without limitation, cyst nematodes and root-knot nematodes. Specific plant parasitic nematodes which are targeted by the present invention include, without limitation, *Heterodera glycines, Heterodera schachtii, Heterodera avenae, Heterodera oryzae, Heterodera cajani, Heterodera trifolii, Globodera pallida, G. rostochiensis*, or *Globodera tabacum, Meloidogyne incognita, M. arenaria, M. hapla, M. javanica, M. naasi, M. exigua, Ditylenchus dipsaci, Ditylenchus angustus, Radopholus similis, Radopholus citrophilus, Helicotylenchus multicinctus, Pratylenchus coffeae, Pratylenchus brachyurus, Pratylenchus vulnus, Paratylenchus curvitatus, Paratylenchus zeae, Rotylenchulus reniformis, Paratrichodorus anemones, Paratrichodorus minor, Paratrichodorus christiei, Anguina tritici, Bidera avenae, Subanguina radicicola, Hoplolaimus seinhorsti, Hoplolaimus Columbus, Hoplolaimus galeatus, Tylenchulus semipenetrans, Hemicycliophora arenaria, Rhadinaphelenchus cocophilus, Belonolaimus longicaudatus, Trichodorus primitivus, Nacobbus aberrans, Aphelenchoides besseyi, Hemicriconemoides kanayaensis, Tylenchorhynchus claytoni, Xiphinema americanum, Cacopaurus pestis*, and the like.

In one embodiment, the targeted nematodes belong to the nematode families inducing feeding cells, giant cells or syncytial cells. Nematode families inducing feeding cells, giant cells or syncytial cells are Longidoridae, Trichodoridae, Heterodidae, Meloidogynidae, Pratylenchidae or Tylenchulidae. Preferably they belong to the family Heterodidae or Meloidogynidae.

Accordingly, in another embodiment the targeted nematodes belong to one or more genus selected from the group of *Cactodera, Dolichodera, Globodera, Heterodera, Punctodera, Longidorus*, or *Meloidogyne*. In a preferred embodiment the targeted nematodes belong to one or more genus selected from the group of *Cactodera, Dolichodera, Globodera, Heterodera, Punctodera*, or *Meloidogyne*. In a more preferred embodiment the targeted nematodes belong to one or more genus selected from the group of *Globodera, Heterodera*, or *Meloidogyne*. In an even more preferred embodiment the targeted nematodes belong to one or both genus selected from the group of *Globodera* or *Heterodera*. In another embodiment the targeted nematodes belong to the genus *Meloidogyne*.

The genus *Globodera* and *Heterodera* are preferred genus in the nematode family Heterodidae. Accordingly n one embodiment the targeted nematode belongs to one or more species selected from the group of *Globodera achilleae, Globodera artemisiae, Globodera hypolysi, Globodera mexicana, Globodera millefolii, Globodera mali, Globodera pallida, Globodera rostochiensis, Globodera tabacum* and *Globodera virginiae*. In a preferred embodiment the targeted nematodes belongs to at least one of the species *Globodera pallida, Globodera tabaccum* or *Globodera rostochiensis*. Accordingly, in one embodiment the targeted nematode belongs to one or more species selected from the group of *Hederodera avenae, Heterodera carotae, Heterodera ciceri, Heterodera cruciferae, Heterodera delvii, Heterodera elachista, Heterodera filipjevi, Heterodera gambiensis, Heterodera glycines, Heterodera goettingiana, Heterodera graduni, Heterodera humuli, Heterodera hordecalis, Heterodera latipons, Heterodera major, Heterodera medicaginis, Heterodera oryzicola, Heterodera pakistanensis, Heterodera rosii, Heterodera sacchari, Heterodera schachtii, Heterodera sorghi, Heterodera trifolii, Heterodera urticae, Heterodera vigni* and *Heterodera zeae*. In a preferred embodiment the targeted nematodes belongs to at least one of the species *Heterodera glycines, Heterodera avenae, Heterodera cajani, Heterodera gottingiana, Heterodera trifolii, Heterodera zeae* or *Heterodera schachtii*. In a more preferred embodiment the targeted nematodes belongs to the species *Heterodera glycines* or *Heterodera schachtii* or to both. In a most preferred embodiment the targeted nematodes belong to the species *Heterodera glycines*.

The genus *Meloidogyne* is a preferred genus in the nematode family Meloidogynidae. Accordingly, in one embodiment the targeted nematode belongs to one or more species selected from the group of *Meloidogyne acronea, Meloidogyne arabica, Meloidogyne arenaria, Meloidogyne artiellia, Meloidogyne brevicauda, Meloidogyne camelliae, Meloidogyne chitwoodi, Meloidogyne cofeicola, Meloidogyne esigua, Meloidogyne graminicola, Meloidogyne hapla, Meloidogyne incognita, Meloidogyne indica, Meloidogyne inornata, Meloidogyne javanica, Meloidogyne lini, Meloidogyne mali, Meloidogyne microcephala, Meloidogyne microtyla, Meloidogyne naasi, Meloidogyne salasi* and *Meloidogyne thamesi*. In a preferred embodiment the targeted nematodes belongs at least one of the species *Meloidogyne javanica, Meloidogyne incognita, Meloidogyne hapla, Meloidogyne arenaria* or *Meloidogyne chitwoodi*.

Plants which may be protected by nucleic acid constructs containing the promoters of the present invention include, without limitation, a genus selected from the group consisting of *Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Zea, Triticum, Triticale, Secale, Lolium, Hordeum, Glycine, Pseudotsuga, Kalanchoe, Beta, Helianthus, Nicotiana, Cucurbita, Rosa, Fragaria, Lotus, Medicago, Onobrychis, trifolium, Trigonella, Vigna, Citrus, Linum, Geranium, Manihot, Daucus, Raphanus, Sinapis, Atropa, Datura, Hyoscyamus, Nicotiana, Petunia, Digitalis, Majorana, Ciahorium, Lactuca, Bromus, Asparagus, Antirrhinum, Heterocallis, Nemesis, Pelargonium, Panieum, Pennisetum, Ranunculus, Senecio, Salpiglossis, Browaalia, Phaseolus, Avena*, and *Alliumi*.

Some derivatives and variants of the promoter polynucleotides are preferably be used in particular plant clades, families, genus or plant species. Derivatives and variants of the promoter polynucleotides, which can be isolated from one plant species are preferably used in plants of the same clade, family, genus or species of plants of which the plant, used for isolation of the derivative and variant of the promoter polynucleotides, belongs to. Accordingly in one embodiment the plant is a monocotyledonous plant, preferably a plant of the family Poaceae, Musaceae, Liliaceae or Bromeliaceae, preferably of the family Poaceae. Accordingly, in yet another embodiment the plant is a Poaceae plant of the genus *Zea, Triticum, Oryza, Hordeum. Secale, Avena, Saccharum, Sorghum, Pennisetum, Setaria, Panicum, Eleusine, Miscanthus, Brachypodium, Festuca* or *Lolium*. Accordingly, in another embodiment the plant of the genus *Zea*, preferably of the species *Zea mays*. Accordingly, in one embodiment the plant is of the genus *Triticum*, preferably of the species *Triticum aestivum, Triticum speltae* or *Triticum durum*. Accordingly, in one embodiment the plant is of the genus *Oryza*, preferably of the species *Oryza sativa*. Accordingly, in one embodiment the plant is of the genus *Hordeum*, preferably of the species *Hordeum vulgare*. Accordingly, in one embodiment the plant is of the genus *Secale*, preferably of the species *Secale cereale*. Accordingly, in one embodiment the plant is of the genus *Avena*, preferably of the species *Avena sativa*. Accordingly, in one embodiment the plant is of the genus *Saccarum*, preferably of the species *Saccharum officinarum*. Accordingly, in one embodiment the plant is of the genus *Sorghum*, preferably of the species *Sorghum vulgare, Sorghum bicolor* or *Sorghum sudanense*. Accordingly, in one embodiment the plant is of the genus *Pennisetum*, preferably of the species *Pennisetum glaucum*. In one embodiment the plant is of the genus *Setaria*, preferably of the species *Setaria italica*. Accordingly, in one embodiment the plant is of the genus *Panicum*, preferably of the species *Panicum miliaceum* or *Panicum virgatum*. Accordingly, in one embodiment the plant is of the genus *Eleusine*, preferably of the species *Eleusine coracana*. Accordingly, in one embodiment the plant is of the genus *Miscanthus*, preferably of the species *Miscanthus sinensis*. Accordingly, in one embodiment the plant is of the genus *Brachypodium*, preferably of the species *Brachypodium distachyon*. Accordingly, in one embodiment the plant is a plant of the genus *Festuca*, preferably of the species *Festuca arundinaria, Festuca rubra* or *Festuca pratensis*. Accordingly, in one embodiment the plant is a plant of the genus *Lolium*, preferably of the species *Lolium perenne* or *Lolium multiflorum*. Accordingly, in one embodiment the plant is Triticosecale.

Accordingly, in one embodiment the plant is a dicotyledonous plant, preferably a plant of the family Fabaceae, Solanaceae, Brassicaceae, Chenopodiaceae, Asteraceae, Malvaceae, Linacea, Euphorbiaceae, Rosaceae, Cucurbitaceae, Theaceae, Rubiaceae, Sterculiaceae or Citrus. In one embodiment the plant is a plant of the family Fabaceae, Solanaceae or Brassicaceae. Accordingly, in one embodiment the plant is of the family Fabaceae, preferably of the genus *Glycine, Pisum, Arachis, Cicer, Vicia, Phaseolus, Lupinus, Medicago* or *Lens*. Preferred species of the family Fabaceae are *Glycine max, Pisum sativum, Arachis hypogea, Cicer arietinum, Vicia faba, Phaseolus vulgaris, Lupinus albus, Lupinus luteus, Lupinus angustifolius, Medicago sativa* or *Lens culinaris*. More preferred is the species *Glycine max*.

Accordingly, in one embodiment the plant is of the family Solanaceae, preferably of the genus *Solanum, Lycopersicon, Nicotiana* or *Capsicum*. Preferred species of the family Solanaceae are *Solanum tuberosum, Lycopersion esculentum, Nicotiana tabaccum* or *Capsicum chinense*. More preferred is *Solanum tuberosum*. Accordingly, in one embodiment the plant is of the family Brassicaceae, preferably of the genus *Arabidopsis, Brassica* or *Raphanus*. Preferred species of the family Brassicaceae are the species *Arabidopsis thaliana, Brassica napus, Brassica oleracea, Brassica juncea* or *Brassica rapa*. More preferred is the species *Brassica napus*. Accordingly, in one embodiment the plant is of the family Chenopodiaceae, preferably of the genus *Beta*. A preferred species of the genus *Beta* is the species *Beta vulgaris*. Accordingly, in one embodiment the plant is of the family Asteraceae, preferably of the genus *Helianthus* or *Tagetes*. Preferred species of the of the genus *Helianthus* is the species *Helianthus annuus* a preferred species of the genus *Tagetes* is the species *Tagetes erecta*. Accordingly, in one embodiment the plant is of the family Malvaceae, preferably of the genus *Gossypium* or *Abelmoschus*, Preferred species of the genus *Gossypium* are the species *Gossypium hirsutum* or *Gossypium barbadense*. More preferred is the species *Gossypium hirsutum*. A preferred species of the genus *Abelmoschus* is the species *Abelmoschus esculentus*. Accordingly, in one embodiment the plant is of the family Linacea, preferably of the genus *Linum*. A preferred species of the genus *Linum* is the species *Linum usitatissimum*. Accordingly, in one embodiment the plant is of the family Euphorbiaceae, preferably of the genus *Manihot, Jatropa, Rhizinus* or *Ipomea*. Preferred species of the genus is the species *Manihot esculenta*. A preferred species of the genus *Jatropa* is *Jatropa curca*. A preferred species of the genus *Rhizinus* is *Rhizinus comunis* A preferred species of the genus *Ipomea* is *Ipomea batatas*. Accordingly, in one embodiment the plant is of the family Rosaceae, preferably of the genus *Rosa, Malus, Pyrus, Prunus, Rubus, Ribes, Vaccinium,* or *Fragaria*. A preferred species of the genus *Fragaria* is the hybrid *Fragaria×ananassa*. Accordingly, in one embodiment the plant is of the family Cucurbitaceae, preferably of the genus *Cucumis, Cirullus* or *Cucurbita*. Preferred species of the genus *Cucumis* is the species *Cucumis sativus*. A preferred species of the genus *Citrullus* is *Citrullus* lanatus. A preferred species of the genus *Cucurbita* is *Cucurbita pepo*. Accordingly, in one embodiment the plant is of the family Theaceae, preferably of the genus *Camellia*. A preferred species of the genus *Camellia* is the species *Camellia sinensis*. Accordingly, in one embodiment the plant is of the family Rubiaceae, preferably of the genus *Coffea*. A preferred species of the genus *Coffea* are the species *Coffea arabica* or *Coffea canephora*. Accordingly, in one embodiment the plant is of the family Sterculiaceae, preferably of the genus *Theobroma*. A preferred species of the genus *Theobroma* is the species *Theobroma cacao*. Accordingly, in one embodiment the plant is of the genus *Citrus*, preferably of the *Citrus* species and hybrids planted in close proximity or plantations, like *Citrus sinensis, Citrus limon, Citrus reticulata, Citrus maxima*, or the like.

The *Arabidopsis* promoter (SEQ ID NO:1) represents the promoter region of *Arabidopsis* At5g05340 gene. The soybean cDNA clone 59712764 of this invention (SEQ ID NO:2,) was isolated from soybean RNA as disclosed in Example 1 and shows significant alignment at the amino acid level with the protein encoded by At5g05340. As demonstrated in Example 3, when the *Arabidopsis* promoter was placed in operative association with a GUS reporter gene, the GUS gene expression was up-regulated in soybean hairy roots infected by nematodes.

The invention is thus embodied in a promoter comprising an promoter polynucleotide having the sequence as set forth in SEQ ID NO:1, or a minimal promoter polynucleotide fragment derived from an isolated nucleic acid having the sequence as set forth in SEQ ID NO:1 which is capable of mediating root-specific or nematode-inducible expression of a second polynucleotide. The methods disclosed herein may be employed to isolate additional minimal promoter polynucleotide fragments of SEQ ID NO:1 which are capable of mediating root-specific and/or nematode-inducible expression of a second polynucleotide.

Alternatively, the promoter polynucleotide of the invention comprises an isolated polynucleotide which hybridizes under stringent conditions to a polynucleotide having the sequence as set forth in SEQ ID NO:1, or a minimal promoter polynucleotide fragment derived from a polynucleotide having the sequence as set forth in SEQ ID NO:1. Stringent hybridization conditions as used herein are well known, including, for example, 400 mM NaCl, 40 mM PIPES pH 6.4, 1 mM EDTA, 60° C. hybridization for 12-16 hours; followed by washing in 0.1% SDS, 0.1% SSC at approximately 65° C. for about 15-60 minutes. The invention is further embodied in an isolated polynucleotide that hybridizes under stringent conditions to a polynucleotide comprising nucleotides 1677 to 2027 or nucleotides 1604 to 2085 of a sequence as set forth in SEQ ID NO:1, wherein the promoter polynucleotide is induced in roots of a plant by plant parasitic nematodes. The promoter polynucleotides of the invention further comprises an isolated polynucleotide which has at least 50-60%, or at least 60-70%, or at least 70-80%, 80-85%, 85-90%, 90-95%, or at least 95%, 96%, 97%, 98%, 99% or more identical or similar to a nucleic acid having a sequence as set forth in SEQ ID NO; 1, or a minimal promoter polynucleotide fragment derived from a sequence as set forth in SEQ ID NO:1. The length of the sequence comparison for polynucleotides is at least 50 consecutive nucleotides, or at least 100 consecutive nucleotides, or at least 200 consecutive nucleotides up to the whole length of the sequence.

The term "sequence identity" or "identity" in the context of two polynucleotide or polypeptide sequences makes reference to those positions in the two sequences where identical pairs of symbols fall together when the sequences are aligned for maximum correspondence over a specified comparison window, for example, either the entire sequence as in a global alignment or the region of similarity in a local alignment. When percentage of sequence identity is used in reference to polypeptides it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skilled in the art. Typically this involves scoring a conservative substitution as a partial match rather than a mismatch, thereby increasing the percentage of sequence similarity.

As used herein, "percentage of sequence identity" or "sequence identity percentage" denotes a value determined by first noting in two optimally aligned sequences over a comparison window, either globally or locally, at each constituent position as to whether the identical nucleic acid base or amino acid residue occurs in both sequences, denoted a match, or does not, denoted a mismatch. As said alignment are constructed by optimizing the number of matching bases, while concurrently allowing both for mismatches at any position and for the introduction of arbitrarily-sized gaps, or null or empty regions where to do so increases the significance or quality of the alignment, the calculation determines the total number of positions for which the match condition exists, and then divides this number by the total number of positions in the window of comparison, and lastly multiplies the result by 100 to yield the percentage of sequence identity. "Percentage of sequence similarity" for protein sequences can be calculated using the same principle, wherein the conservative substitution is calculated as a partial rather than a complete mismatch. Thus, for example, where an identical amino acid is given a score of 1 and a non-conservative substitution is given a score of zero, a conservative substitution is given a score between zero and 1. The scoring of conservative substitutions can be obtained from amino acid matrices known in the art, for example, Blosum or PAM matrices.

Methods of alignment of sequences for comparison are well known in the art. The determination of percent identity or percent similarity (for proteins) between two sequences can be accomplished using a mathematical algorithm. Preferred, non-limiting examples of such mathematical algorithms are, the algorithm of Myers and Miller (Bioinformatics, 4(1):11-17, 1988), the Needleman-Wunsch global alignment (J. Mol. Biol., 48(3):443-53, 1970), the Smith-Waterman local alignment (J. Mol. Biol., 147:195-197, 1981), the search-for-similarity-method of Pearson and Lipman (PNAS, 85(8): 2444-2448, 1988), the algorithm of Karlin and Altschul (Altschul et al., J. Mol. Biol., 215(3):403-410, 1990; PNAS, 90:5873-5877, 1993). Computer implementations of these mathematical algorithms can be utilized for comparison of sequences to determine sequence identity or to identify homologs.

The invention further embodies "variants" or "derivatives" of the promoter polynucleotides of the invention. Derivatives of the specific promoter polynucleotide sequences and their specific elements may include, but are not limited to, deletions of sequence, single or multiple point mutations, alterations at a particular restriction enzyme site, addition of functional elements, or other means of molecular modification. This modification may or may not enhance, or otherwise alter the transcription regulating activity of said sequences.

For example, one of skill in the art may delimit the functional elements or biologically active portions within the sequences and delete any non-essential elements. Functional elements or biologically active potions may be modified or combined to increase the utility or expression of the sequences of the invention for any particular application. Functionally equivalent fragments of a promoter polynucleotide of the invention can also be obtained by removing or deleting non-essential sequences without deleting the essential one. Narrowing the promoter polynucleotide sequence to its essential, transcription mediating elements can be realized in vitro by trial-and-error deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002). Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences. The term "minimal promoter" as used herein refers to a biologically active portion of a promoter polynucleotide that is cable of mediating root-specific and/or nematode-inducible expression of a second nucleic acid. Specific minimal promoter polynucleotide fragments of the invention include, without limitation, a polynucleotide comprising nucleotides 1677 to 2027 or nucleotides 1604 to 2085 of a sequence as set forth in SEQ ID NO:1, a polynucleotide comprising a fragment of at least 50 consecutive nucleotides, or at least 100 consecutive nucleotides, or at least 200 consecutive nucleotides of a polynucleotide having the sequence as set forth in SEQ ID NO:1.

As indicated above, deletion mutants of the promoter polynucleotide of the invention also could be randomly prepared and then assayed. With this strategy, a series of constructs are prepared, each containing a different portion of the clone (a subclone), and these constructs are then screened for activity. A suitable means for screening for activity is to attach a deleted promoter construct, which contains a deleted segment to a selectable or screenable marker, and to isolate only those cells expressing the marker gene. In this way, a number of different, deleted promoter constructs are identified which still retain the desired, or even enhanced, activity. The smallest segment, which is required for activity, is thereby identified through comparison of the selected constructs. This segment may then be used for the construction of vectors for the expression of exogenous genes.

The means for mutagenizing or creating deletions in a DNA segment encoding any promoter sequence are well known to those of skill in the art and are disclosed, for example, in U.S. Pat. No. 6,583,338, incorporated herein by reference in its entirety. One example of a regulatory sequence variant is a promoter formed by one or more deletions from a larger promoter. The 5' portion of a promoter up to the TATA box near the transcription start site can sometimes be deleted without abolishing promoter activity, as described by Zhu et al., (1995) The Plant Cell 7:1681-1689. A routine way to remove part of a DNA sequence is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Biologically active variants also include, for example, the native promoter sequences of the invention having one or more nucleotide substitutions, deletions or insertions.

Derivatives and variants also include homologs, paralogs and orthologs from other species, such as but not limited to, bacteria, fungi, and plants. "Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Paralog" refers to a polynucleotide or polypeptide that within the same species which is functionally similar. "Ortholog" refers to a polynucleotide or polypeptide that is the functional equivalent of the polynucleotide or polypeptide in another species. An orthologous gene means preferably a gene, which is encoding an orthologous protein. More specifically, the term "ortholog" denotes a polypeptide or protein obtained from one species that is the functional counterpart of a polypeptide or protein from a different species. Sequence differences among orthologs are the result of speciation.

One of the embodiments encompasses allelic variants of a promoter polynucleotide capable of mediating root-preferred and/or nematode-inducible expression selected from the group consisting of a) a polynucleotide having the sequence as set forth in SEQ ID NO:1; b) a polynucleotide comprising nucleotides 1677 to 2027 or nucleotides 1604 to 2085 of a polynucleotide having the sequence as set forth in SEQ ID NO:1; c) a polynucleotide having at least 70% sequence identity to the polynucleotide of a) or b); d) a polynucleotide hybridizing under stringent conditions to the polynucleotide of a) or b); e) a polynucleotide comprising a biologically active portion of the polynucleotide of a) or b); and h) a polynucleotide comprising a fragment of at least 50 consecutive nucleotides, or at least 100 consecutive nucleotides, or at least 200 consecutive nucleotides of a polynucleotide having the sequence as set forth in SEQ ID NO:1. As used herein, the term "allelic variant" refers to a promoter polynucleotide containing polymorphisms that lead to changes in the nucleotides of the polynucleotide and that exist within a natural population (e.g., a plant species or variety). The term "allelic variant" also refers to a polynucleotide containing polymorphisms that lead to changes in the amino acid sequences of a protein encoded by the nucleotide and that exist within a natural population. Such natural allelic variations can typically result in 1-5% variance in a polynucleotide, or 1-5% variance in the encoded protein. Allelic variants can be identified by sequencing the nucleic acid of interest in a number of different plants, which can be readily carried out by using, for example, hybridization probes to identify the same gene genetic locus in those plants. Any and all such nucleic acid variations in a polynucleotide are the result of natural allelic variation and that do not alter the functional activity of the polynucleotide are intended to be within the scope of the invention.

The invention is also embodied in expression cassettes comprising the promoters polynucleotides of the invention. "Expression cassette" in this context is to be understood broadly as comprising all sequences contained in the cassette which may influence transcription of a polynucleotide of interest and, if applicable, translation thereof. In addition to the promoters polynucleotide of the invention, the expression cassette of the invention may further comprise regulatory elements that improve the function of the promoter polynucleotide, genetic elements that allow transcription and/or translation in prokaryotic and/or eukaryotic organisms, and downstream (in 3'-direction) regulatory elements such as a transcription termination sequence and a polyadenylation sequence. The various components of the expression cassette of the invention are sequentially and operably linked together.

Accordingly, an expression cassette of the invention may comprise a promoter polynucleotide capable of mediating root-preferred or nematode-inducible expression selected from the group consisting of a) a polynucleotide having the sequence as set forth in SEQ ID NO:1; b) a polynucleotide comprising nucleotides 1677 to 2027 or nucleotides 1604 to 2085 of a polynucleotide having the sequence as set forth in SEQ ID NO:1; c) a polynucleotide having at least 70% sequence identity to the polynucleotide of a) or b); d) a polynucleotide hybridizing under stringent conditions to the polynucleotide of a) or b); e) a polynucleotide comprising a biologically active portion of the polynucleotide of a) or b); and f) a polynucleotide comprising a fragment of at least 50 consecutive nucleotides, or at least 100 consecutive nucleotides, or at least 200 consecutive nucleotides of a polynucleotide having the sequence as set forth in SEQ ID NO:1. In another embodiment, the promoter is induced in roots of a plant infected by plant parasitic nematodes. An infection with plant parasitic nematodes usually results in a nematode stimulus. The promoter polynucleotides of the invention induce transcription of a operably linked polynucleotide in the plant cell in response to a nematode stimulus.

The term root-preferred expression in regard to promoters polynucleotides of the invention means expression in root-tissue, in particular in root vascular tissue.

Specific genetic elements that may optionally be included in the expression cassette of the invention include, without limitation, origins of replication to allow replication in bacteria, e.g., the ORI region from pBR322 or the P15A ori; or elements required for *Agrobacterium* T-DNA transfer, such as, for example, the left and/or right borders of the T-DNA. Other components of the expression cassette of the invention may include, without limitation, additional regulatory elements such as, for example, enhancers, introns, polylinkers, multiple cloning sites, operators, repressor binding sites, transcription factor binding sites, and the like. Exemplary enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Exemplary plant intron sequences include introns from Adh1, bronze1, actin1, actin 2 (WO 00/760067), or the sucrose synthase intron; see: The Maize Handbook, Chapter 116, Freeling and Walbot, Eds., Springer, N.Y. (1994).

Viral leader sequences may also enhance transcription of nucleic acids of interest by the expression cassette of the invention. For example, leader sequences from Tobacco Mosaic Virus (TMV), Maize Chlorotic Mottle Virus (MCMV), and Alfalfa Mosaic Virus (AMV) have been shown to be effective in enhancing expression. Other leaders known in the art include but are not limited to: Picornavirus leaders, for example, (Encephalomyocarditis virus (EMCV) leader; Potyvirus leaders, Tobacco Etch Virus (TEV) leader; MDMV leader (Maize Dwarf Mosaic Virus); Human immunoglobulin heavy-chain binding protein (BiP) leader, Untranslated leader from the coat protein mRNA of alfalfa mosaic virus (AMV RNA 4).

The expression cassette of the invention also comprises a transcription termination element or polyadenylation signal. Exemplary transcription termination elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

A second polynucleotide to be transcribed into RNA, and, optionally, expressed as a protein is inserted into the expression cassette of the invention for transformation into an organism. In accordance with the invention, the second polynucleotide is placed downstream (i.e., in 3'-direction) of the promoter of the invention and upstream of the transcription termination elements, in covalent linkage therewith. Preferably, the distance between the second polynucleotide and the promoter of the invention is not more than 200 base pairs, more preferably not more than 100 base pairs, most preferably not more than 50 base pairs.

An expression cassette of the invention may also be assembled by inserting a promoter of the invention into the plant genome. Such insertion will result in an operable linkage to a nucleic acid sequence of interest native to the genome. Such insertions allow the nucleic acid of interest to be expressed or over-expressed preferentially in root tissue, after induction by nematodes, as the result of the transcription regulating properties of the promoter of the invention. The insertion may be directed or by chance. Preferably, the insertion is directed and realized, for example, by homologous recombination. By this procedure a natural promoter may be replaced by the promoter of the invention, thereby modifying the expression profile of an endogenous gene.

The expression cassette of the invention may be inserted into a recombinant vector, plasmid, cosmid, YAC (yeast artificial chromosome), BAC (bacterial artificial chromosome), or any other vector suitable for transformation into host cell. Preferred host cells are bacterial cells, in particular *Escherichia coli, Agrobacterium tumefaciens* and *Agrobacterium rhizogenes* cells, and plant cells. When the host cell is a plant cell, the expression cassette or vector may become inserted into the genome of the transformed plant cell. Alternatively, the expression cassette or vecfor may be maintained extra chromosomally. The expression cassette or vector of the invention may be present in the nucleus, chloroplast, mitochondria, and/or plastid of the cells of the plant. Preferably, the expression cassette or vector of the invention is inserted into the chromosomal DNA of the plant cell nucleus.

The expression cassette of the invention may be transformed into a plant to provide a transgenic plant comprising one or more polynucleotides in operative association with a promoter polynucleotide of the invention. The transgenic plant of this embodiment comprises a promoter comprising a polynucleotide sequence as set forth in SEQ ID NO:1 or a minimal promoter polynucleotide fragment of SEQ ID NO:1. Alternatively, the transgenic plant of the invention comprises a polynucleotide that hybridizes under stringent conditions to a promoter comprising a nucleic acid sequence as set forth in SEQ ID NO:1, or a minimal promoter polynucleotide fragment of SEQ ID NO:1. Further, the transgenic plant of the invention comprises a promoter nucleotide having at least 70% sequence identity to a polynucleotide having the sequence as set forth in SEQ ID NO:1, or a minimal promoter polynucleotide fragment of SEQ ID NO:1.

The transgenic plants of the invention are made using transformation methods known to those of skill in the art of plant biotechnology. Any method may be used to transform the recombinant expression vector into plant cells to yield the transgenic plants of the invention. Suitable methods for transforming or transfecting host cells including plant cells can be found, for example, in WO2006/024509 (PCT/EP2005/009366; U.S. Ser. No 60/6060789) and in Sambrook et al. supra, and in other laboratory manuals such as Methods in Molecular Biology, 1995, Vol. 44, *Agrobacterium* protocols, Ed: Gartland and Davey, Humana Press, Totowa, N.J.

General methods for transforming dicotyledenous plants are also disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824,877; 6,384,301 and in EP 0301749B1. Other plant transformation methods are disclosed, for example, in U.S. Pat. Nos. 4,945,050; 5,188,958; 5,596,131; 5,981,840, and the like.

The term "plant" as used herein can, depending on context, be understood to refer to whole plants, plant cells, plant organs, plant seeds, and progeny of same. The word "plant" also refers to any plant, particularly, to seed plant, and may include, but not limited to, crop plants. Plant parts include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, seeds and the like. The plant can be from a genus selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, and *Arabidopsis thaliana*. In another embodiment the plant can be from a genus selected from the group consisting of, tobacco, sunflower, pea, alfalfa, soybean, tomato, potato, cotton, tobacco, eggplant, pepper, oilseed rape, canola, beet, cabbage, cauliflower, broccoli, lettuce, *Lotus* sp., *Medicago truncatula* and *Arabidopsis thaliana*. In another embodiment the plant can be from a genus selected from the group consisting of maize, wheat, barley, sorghum, rye, triticale, rice, sugarcane, pineapple, coconut, banana, perennial grass and ryegrass.

The transgenic plants of the invention may be crossed with similar transgenic plants or with transgenic plants lacking the promoter of the invention and second nucleic acid or with non-transgenic plants, using known methods of plant breeding, to prepare seed. Further, the transgenic plant of the present invention may comprise, and/or be crossed to another transgenic plant that comprises, one or more different genes of interest operably linked to a promoter polynucleotide of the present invention or to another promoter, thus creating a "stack" of transgenes in the plant and/or its progeny. The seed is then planted to obtain a crossed fertile transgenic plant comprising the nucleic acid of interest and the promoter of the invention. The plant may be a monocot or a dicot. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the DNA construct.

"Gene stacking" can also be accomplished by transferring two or more genes into the cell nucleus by plant transformation. Multiple genes may be introduced into the cell nucleus during transformation either sequentially or in unison. Multiple genes in plants or target pathogen species can be down-regulated by gene silencing mechanisms, specifically RNAi, by using a single transgene targeting multiple linked partial sequences of interest. Stacked, multiple genes under the control of individual promoters can also be over-expressed to attain a desired single or multiple phenotype. Constructs containing gene stacks of both over-expressed genes and silenced targets can also be introduced into plants yielding single or multiple agronomically important phenotypes. In certain embodiments the nucleic acid sequences of the present invention can be stacked with any combination of polynucleotide sequences of interest to create desired phenotypes. The combinations can produce plants with a variety of trait combinations including but not limited to disease resistance, herbicide tolerance, yield enhancement, cold and drought tolerance. These stacked combinations can be created by any method including but not limited to cross breeding plants by conventional methods or by genetic transformation. If the traits are stacked by genetic transformation, the polynucleotide sequences of interest can be combined sequentially or simultaneously in any order. For example if two genes are to be introduced, the two sequences can be contained in separate transformation cassettes or on the same transformation cassette. The expression of the sequences can be driven by the same or different promoters.

The invention further comprises a crop comprising a plurality of the transgenic plants of the invention, planted together in an agricultural field.

The transgenic plants of the invention may be used in a method of controlling a plant parasitic nematode infestation in a crop, which comprises the step of growing said crop from seeds comprising an expression cassette comprising a promoter polynucleotide of the invention in operative association with a second polynucleotide that encodes an agent that disrupts the metabolism, growth and/or reproduction of said plant parasitic nematode, that improves plant tolerance to said plant parasitic nematode, or that is toxic to said plant parasitic nematode, wherein the expression cassette is stably integrated into the genomes of plant cells, plants and/or seeds. Such agents include, without limitation, a double-stranded RNA which is substantially identical to a target gene of a parasitic plant nematode which is essential for survival, metamorphosis, or reproduction of the nematode; a double-stranded RNA which is substantially identical to a plant gene required to maintain a nematode feeding site; an anti-sense RNA, an siRNA, an miRNA or its precursor, a protein that interferes with the metabolism, survival, metamorphosis or reproduction of the nematode, or a microbial toxin, a toxin derived from an insect or any toxin that interferes with the metabolism, survival, metamorphosis or reproduction of the nematode, and the like.

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Example 1

Gene Expression Analysis to Identify SCN Induced Soybean Genes

Soybean *Glycine max* cv. Williams 82 seeds were germinated on 1% agar plates for 3 days at 25° C. and transferred onto germination pouches with one seedling per pouch. One day later, each seedling was inoculated with 1000 second stage juveniles (J2) of *Heterodera glycines* race3. The seedlings were maintained at the same culturing condition. The position of the root tip was marked on the pouch. One day after inoculation, the seedling was taken out and rinsed in water to remove remaining nematodes on the surface, and then transferred onto a new pouch, and the position of the root tip was marked on the pouch.

Six days after inoculation, the root portion between the two marks was sliced into 1 cm long pieces with a razor blade and immediately fixed in a solution containing 3 parts of ethanol and 1 part of glacial acidic acid. The solution was vacuumed at 400 mm Hg for 15 minutes twice and then kept on ice for 4-8 hours. The root pieces were then infiltrated by 10% sucrose for 4 hours on ice and then 15% sucrose for 4 hours on ice. During each infiltration step, the solution was first vacuumed for 15 minutes at 400 mm Hg. All sucrose solutions were DEPC (Sigma-Aldrich Corp., St. Louis, Mo.) treated to suppress RNAase activity.

The root pieces were then picked up and blotted on paper towel to remove the liquid on the surface, and then embedded in OCT (Optimum Cutting Temperature) (Sakura Finetechnical Co., Ltd., Tokyo, Japan) in a cryomold, followed by immediately freezing in liquid nitrogen. Once the OCT formed a block in the mold, it can be stored at −80° C.

The root pieces were sectioned at 10 µm longitudinally with Leica Cryostat C3050s (Leica Microsystems Nussloch GmbH, Nussloch, Germany). The temperature for the cutting is set to −15° C. Sections were transferred onto PEN (P.A.L.M. Microlaser Technologies GmbH, Bernried, Germany) slide on the membrane side and stored at −80° C.

The slides were first fixed in cold (4° C.) 70% Ethanol for 1 minute, then the OCT were dissolved by immersing the slides in 1×PBS (Mediatech Inc., Herndon, Va.) for 2 minutes, followed by dehydration in 70%, 95%, and 100% ethanol for 1 minute in each solution. The slides were then air dried and mounted onto the PALM (P.A.L.M. Microlaser Technologies GmbH, Bernried, Germany) microscope for observation. The syncytia cells were identified by their unique morphology of enlarged cell size, thickened cell wall, and dense cytoplasm. The cap of a 200 µl micro-tube was filled with 20 µl RNA extraction buffer from the kit and mounted over the sample with a holder, with the open end facing the sample. Using the computer interface of the PALM system, the cutting region was defined. Then a laser beam was fired through the slide and cut the syncytium into small pieces. At the same time, the force of the laser bean blew the cut pieces into the RNA extraction buffer above the sample. Once finished, the cap was removed from the holder and recapped onto its tube, and the RNA extraction buffer containing the cut pieces of the syncytia was spun down to the bottom of the tube.

Total cellular RNA was extracted and isolated from laser-captured cells using the PicoPure RNA Isolation Kit from Arcturus (Arcturus Inc., Mountain View, Calif.) following the manufacturer's instruction.

To amplify RNA from low input total RNA, RiboAmp HS RNA Amplification Kit from Arcturus (Arcturus Inc., Mountain View, Calif.) was used following the manufacturer's instruction, including addition of nucleic acid carrier to the input sample RNA prior to the start of RiboAmp HS protocol as recommended in the user guide. Successful amplification was achieved when as little as 500 pg reference RNA together with carrier nucleic acid supplied in the RiboAmp HS RNA Amplification Kit, were used as input in the amplification reaction.

The Soybean (*Glycine max*) cDNA PCR products representing set of genes to be interrogated are spotted robotically onto chemically modified glass support (UltraGAPS, Corning Inc., Acton, Mass.) after purification and re-suspension in 50% DMSO using a Gen III Spotter (Amersham Biosciences, Piscataway, N.J.). A control PCR plate consisted of a set of control genes (18 genes in 12 replicates) was included at the beginning of all spotting sessions, as such, the first 18 spots in the first row of each panel were external spike genes and they can be used as QC controls and/or to obtain a standard curve with which the normalized abundance for the other clones in the panel was calculated. The control genes are a commercially available set of artificial genes designed based upon sequences of the yeast intergenic regions (Amersham Biosciences, Piscataway, N.J.).

The implementation of a set of control genes in the microarray process allowed adoption of a single color-based hybridization approach instead of the previously practiced two-color hybridization format, i.e. labeling and hybridizing a single cDNA sample to a cDNA array instead of a treatment vs reference sample pair. Consequently, normalized signal intensity, and hence absolute transcript abundance for each expressed transcript in the original RNA sample instead of ratios, can be calculated and compared between samples and across different experiments.

The amplified RNA (aRNA) samples were indirectly labeled with Cy 3 using the 3DNA Dendrimer technology of Genisphere™ as described in the random primer-based labeling protocol (Genisphere, Hatfield, Pa.) and hybridized to the soybean cDNA arrays using a two-step hybridization protocol as described in the Mfr's instruction (Genisphere, Hatfield, Pa.). cDNA products from the reverse transcription of aRNA were column-purified and its quality checked on Agilent BioAnalyzer. Purified cDNA was then ligated to capture sequences and further purified and concentrated using standard molecular biological protocols. To increase the reproducibility and cross-sample comparability, identical amount (~250 ng) of purified cDNA-capture sequence ligation mix was used to hybridize the arrays for all samples. Known amount of corresponding cDNA pre-mix for the control genes was spiked into the sample cDNA prior to hybridization and labeling. To minimize variations associated with manual hybridization, all hybridizations were performed on a Lucidea Pro Automated Slide Processor (Amersham Biosciences, Piscataway, N.J.).

Processed slides were scanned using a Gen III Scanner (Amersham Biosciences, Piscataway, N.J.). The .gel files generated from the Gen III Scanner were imported into and analyzed using feature extraction software ImaGene version 5.1 from BioDiscovery (Los Angeles, Calif.) in which images were segmented into pixels and converted to numeric intensity values. Local background and other QC values associated with each spot on the image were also obtained.

Raw data obtained from ImaGene was directly imported into a SAS-based microarray expression data analysis pipeline developed in-house and processed in the following sequential steps.

Data from negative, empty and bad spots were removed from the dataset. The definition of the negative, empty and bad spots followed software developers' recommendation (BioDiscovery, Los Angeles, Calif.) as well as based on empirically determined settings for data removal. Negative spots were defined as any spots with which a negative signal value was obtained after correcting for local background. Empty spots were defined as any spots that had signal values after correcting for local background of less than $n \times SD_{background}$ where n is commonly defined as 2 or 3. Whereas bad spots were defined as any spots with $CV_{Signal\ Intensity}$ greater than an empirically defined value, which is a measure of the spot/signal morphology, foreign contamination and uniformity of the hybridization signal. All the settings have to be set before processing the images in ImaGene software and spots will be tagged a non-zero "flag" value indicative of the type of QC misses in the ImaGene output file. Only spots with a "flag" value of "0" were kept for further analyses. Retained signal measurements were normalized so that the global ground means for each array were scaled to 500.

As a prerequisite to the successful development of an approach for controlling nematode infestations, genes expressed as a result of cyst nematode infestation of soybean roots, need to be identified. These genes include, but are not limited to, genes that are essential for the formation of syncytium and genes differentially expressed in response to SCN infection.

To identify genes specifically and/or differentially expressed in syncytia, three types of cells and root tissues were collected and used for the extraction of total cellular RNA, the syncytia, root segments not in direct contact with soybean cyst nematode but are from SCN infected soybean root designated as "non-syncytia" and untreated control roots. Total RNA was extracted, isolated from LCM captured syncytia and amplified as described above. To isolate total RNA from root segments, TRIZOL RNA isolation kit from Invitrogen Life Technologies (Invitrogen Corporation, Carlsbad, Calif.) was used following manufacturer's recommended protocol. Total RNA was further purified using Qiagen RNeasy Midi kit (Qiagen Inc., Valencia, Calif.) as described in the manufacturer's user guide. To better compare expression data generated from LCM captured syncytia and root tissue segments, total RNA prepared from both "non-syncytia" and untreated control roots were subjected to the same 2-round RNA amplification process as described above, so it was the amplified aRNA from all three cell/tissue types of soybean roots that were compared in the final analysis.

Table 1 provides a list of LCM captured syncytia samples, "non-syncytia", and control root tissues samples collected and analyzed in this study. The information on RNA amplification and microarray hybridization is also included in this table.

TABLE 1

Tissue sample and experimental information

| Treatment | Sample Name | | |
|---|---|---|---|
| | Number of Samples | Number of Amplified RNA | Number of Hybridization |
| 6-Day Syncytia | 2 | 2 | 9 |
| 6-Day Non-Syncytia | 2 | 2 | 11 |
| 6-Day Untreated Roots | 3 | 4 | 17 |

Statistical analyses of gene expression data generated from samples of LCM captured syncytia, "non-syncytia", and control root tissues led to the identification of genes expressed specifically or differentially in syncytia. One such gene, 59712764, is annotated as a peroxidase gene. The table in FIG. 4 summarizes the expression data as measured by cDNA microarray analysis for this gene across all three cell/tissue samples: Syncytia, SCN infected non-syncytia, and untreated control root tissues. Relative levels of gene expression are expressed as normalized signal intensities (± standard deviation).

As demonstrated in FIG. 4, Soybean cDNA clone 59712764 was identified as being up-regulated in syncytia of SCN-infected soybean roots. FIG. 3 depicts the amino acid sequence of soybean cDNA clone 59712764 (SEQ ID NO:3).

Example 2

Cloning an SCN-Inducible Promoter from *Arabidopsis*

The *Arabidopsis* At5g05340 gene was selected based on its similarity to the soybean cDNA clone 59712764 sequence indicated in Example 1. *Arabidopsis* (Columbia ecotype) genomic DNA was extracted using the Qiagen DNAeasy Plant Minikit (Qiagen, Valencia, Calif., US). The 2085 by (SEQ ID NO:1) genomic DNA region (putative promoter sequences) directly upstream of the ATG codon including 5'-untranslated region corresponding to *Arabidopsis* locus identifier At5g05340 was cloned using standard PCR amplification protocols. For this, approximately 0.1 μg of *Arabidopsis* genomic DNA was used as the DNA template in the PCR reaction. The primers used for PCR amplification of the *Arabidopsis* promoter sequences are shown in FIG. 9 and were designed based on the *Arabidopsis* Genomic sequence Database (TAIR). The primer sequences described by SEQ ID NO:5 contains the XmaI restriction site for ease of cloning. The primer sequences described by SEQ ID NO:6 contains the AscI site for ease of cloning. Primer sequences described by SEQ ID NO:5 and SEQ ID NO:6 were used to amplify the promoter region of *Arabidopsis locus* At5g05340.

Amplification reaction mix contained the following: 2.5 µl 10× Hot Start Buffer; 0.15 µl Hot Start Taq DNA polymerase; 0.5 µl 10 mM dNTPs; 0.5 µl 10 µM primer A (SEQ ID NO:5); 0.5 µl 10 mM primer B (SEQ ID NO:6); 1.0 µl Columbia *Arabidopsis* genomic DNA (approximately 100 ng); 19.85 µl water. T3 Thermocycler (Biometra, Goettingen, Germany) was used for the amplification using the following setting: 1 cycle with 900 seconds at 94° C.; 5 cycles with 30 seconds at 94° C., 30 seconds at 52° C., and 120 seconds at 72° C.; 30 cycles with 30 seconds at 94° C., 30 seconds at 62° C., and 120 seconds at 72° C.; 1 cycle with 300 seconds at 72° C. The amplified DNA fragment size for each PCR product was verified by standard agarose gel electrophoresis and the DNA extracted from gel by Qiagen Gel Extraction Kit (Qiagen, Valencia, Calif., US). The purified fragments were cloned into pCR2.1 using the TOPO TA cloning kit following the manufacturer's instructions (Invitrogen). The cloned fragments were sequenced using an Applied Biosystem 373A (Applied Biosystems, Foster City, Calif., US) automated sequencer and verified to be the expected sequence by using the sequence alignment ClustalW (European Bioinformatics Institute, Cambridge, UK) from the sequence analysis tool Vector NTI (Invitrogen, Carlsbad, Calif., US). The 2085 by DNA fragment corresponding to the promoter regions of At5g05340 is shown as SEQ ID NO:1. The restriction sites introduced in the primers for facilitating cloning are not included in the sequences.

Example 3

Binary Vector Construction for Transformation and Generation of Transgenic Hairy Roots To evaluate the expression activity of the cloned promoter, nucleotides 1-2085 of SEQ ID NO:1 were cloned upstream of a GUS reporter gene (bacterial β-glucuronidase or GUS gene (Jefferson (1987) EMBO J. 6, 3901-3907) to create the binary vector "pAW283". The plant selectable marker in the binary vector is a herbicide-resistant form of the acetohydroxy acid synthase (AHAS: EC 4.1.3.18, also known as acetolactate synthase or ALS) gene from *Arabidopsis thaliana* driven by the native *Arabidopsis* AHAS promoter (Sathasivan et al., Plant Phys. 97:1044-50, 1991). ARSENAL (imazapyr, BASF Corp, Florham Park, N.J.) was used as the selection agent.

In the present example, binary vector pAW283 was transformed into *A. rhizogenes* K599 strain by electroporation (Cho et. al., (1998) Plant Sci. 138, 53-65). The transformed *Agrobacterium* was used to induce soybean hairy-root formation using the following protocol. Approximately five days before *A. rhizogenes* inoculation, seeds from soybean cultivar Williams 82 (SCN-susceptible) were sterilized with 10% bleach for 10 minutes and germinated on 1% agar at 25° C. with 16-hour/day lighting. Approximately three days before *A. rhizogenes* inoculation, a frozen stock of *A. rhizogenes* Strain K599 containing the binary vector was streaked on LB+kanamycin (50 µg/ml) plates and incubated at 28° C. in darkness. Approximately one day before *A. rhizogenes* inoculation, a colony was picked from the plate and inoculated into liquid LB+kanamycin (50 µg/ml). The culture was shaken at 28° C. for approximately 16 hours. The concentration of *A. rhizogenes* in the liquid culture was adjusted to OD600=1.0.

Cotyledons were excised from soybean seedlings and the adaxial side was wounded several times with a scalpel. 15 µl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml carbenicillin (to suppress *A. rhizogenes*) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing carbenicillin 500 µg/ml but not ARSENAL.

Example 4

Detection of Promoter Activity in Soybean Hairy Roots

As set forth in Example 3, one of the promoters of the invention was placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

To study the promoter activity of SEQ ID NO:1 in the presence and absence of nematode infection, several independent transgenic lines were generated from transformation with pAW283. Approximately three weeks after subculturing, the transgenic hairy-root lines on MS, were inoculated with surface-decontaminated J2 of SCN race 3 at the 2000 J2/plate level. At 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. After GUS staining, the roots were stained in acid fuchsin and then destained to visualize the nematodes, which were stained red. The roots were then observed under a microscope for detection of GUS expression.

For each transgenic line, 10 randomly picked syncytia were observed and scored for intensity of GUS expression at 12 days after infection (DAI). The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining. The results for lines transformed with pAW283 are presented in FIG. 7.

The result of the GUS staining indicates that for most lines tested, the promoter fragment in pAW283 showed GUS expression in the syncytia at 12 DAI. In contrast, GUS expression in other root parts such as root tips, vascular tissue, and root cortex was undetected.

Example 5

Cloning Deletions of At5g05340 (SEQ ID NO:1) Promoter

In order to more accurately define the promoter region of At5g05340 (SEQ ID NO:1), shorter fragments of the sequence were tested. Plasmid DNA of pAW283 was extracted from E. coli using the Qiagen Plasmid miniprep kit (Qiagen). The 1455 by and 482 by promoter deletion fragments of A. thaliana locus At5g05340 promoter (SEQ ID NO:1) contained in pAW283 were cloned using existing cloning sites contained in pAW283. The 1455 by promoter deletion of At5g05340 (SEQ ID NO:1) was created by digesting pAW283 DNA with the restriction enzymes PstI and SalI. For this, 5 ul of pAW283qcz plasmid DNA (approximately 1 microgram) was digested with 10 units the restriction enzymes PstI and SalI. The 1455 by promoter fragment of pAW283 was then cloned into a vector containing AHAS selection. Subsequently, the GUS gene was cloned into this vector to create RAW448. The 1455 by promoter fragment contained in RAW448 corresponds to bases 631 to 2085 of At5g05340 promoter contained in SEQ ID NO:1. The 482 by promoter deletion construct was derived by digesting pAW283 with XmaI. For this, 5 ul of pAW283 plasmid DNA (approximately 1 microgram) was digested with 10 units the restriction enzymes XmaI. The digest was run on an agarose gel to separate the 5' 1603 by of the At5g05340 promoter in pAW283. The XmaI fragment of pAW283 containing everything except for the 5' 1603 by of the At5g05340 promoter was re-ligated together resulting in RAW437. The 482 by promoter fragment contained in RAW437 corresponds to bases 1604 to 2085 of At5g05340 promoter contained in SEQ ID NO:1

Example 6

Binary Vector Construction At5g05340 Promoter Deletions for Transformation and Generation of Transgenic Hairy Roots To evaluate the expression activity of the cloned promoter deletions derived from pAW283, gene fragments corresponding to nucleotides 631 to 2085 of SEQ ID NO:1 and 1604 to 2085 of SEQ ID NO:1 were cloned upstream of a GUS reporter gene to create the binary vectors "RAW448" and "RAW437", respectively. The plant selection marker in the binary vectors was a mutated AHAS gene from A. thaliana that conferred tolerance to the herbicide ARSENAL (imazapyr, BASF Corporation, Florham Park, N.J.). The selectable marker mutated AHAS was driven by the Arabidopsis AHAS promoter.

Binary vectors pAW2803, RAW448 and RAW437 were transformed into A. rhizogenes K599 strain by electroporation. The transformed Agrobacterium was used to induce soybean hairy-root formation using the following protocol. Approximately five days before A. rhizogenes inoculation, seeds from soybean cultivar Williams 82 (SCN-susceptible) were sterilized with 10% bleach for 10 minutes and germinated on 1% agar at 25° C. with 16-hour/day lighting. Approximately three days before A. rhizogenes inoculation, a frozen stock of A. rhizogenes Strain K599 containing the binary vector was streaked on LB+kanamycin (50 µg/ml) plates and incubated at 28° C. in darkness. Approximately one day before A. rhizogenes inoculation, a colony was picked from the plate and inoculated into liquid LB+kanamycin (50 µg/ml). The culture was shaken at 28° C. for approximately 16 hours. The concentration of A. rhizogenes in the liquid culture was adjusted to $OD_{600}=1.0$.

Cotyledons were excised from soybean seedlings and the adaxial side was wounded several times with a scalpel. 15 µl of A. rhizogenes suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml Carbenicillin (to suppress A. rhizogenes) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 µg/ml but not ARSENAL.

Example 7

Detection of Promoter Deletion Activity in Soybean Hairy Roots

As set forth in Example 6, the promoters of the invention were placed in operative association with the GUS reporter gene to determine their expression activity. The β-glucuronidase activity of the GUS gene can be detected in planta by means of a chromogenic substance such as 5-bromo-4-chloro-3-indoyl-β-D-glucuronic acid (x-Gluc) in an activity staining reaction.

To study the promoter activity of the deletion fragments of SEQ ID NO:1 in the presence and absence of nematode infection, several independent transgenic lines were generated from transformation with pAW283, RAW448, and RAW437. Approximately three weeks after subculturing, the transgenic hairy-root lines on MS were inoculated with surface-decontaminated J2 of SCN race 3 at the 2000 J2/plate level. At 12 days after inoculation (DAI), the roots were harvested by removing from the agar plates and gently rinsed with changes in water and stained in GUS staining solution containing X-Gluc (2 mg/l) at 37° C. for 16 hours. At each time point after inoculation, a non-inoculated control plate from each line was also stained in GUS staining solution. After GUS staining, the roots were stained in acid fuchsin and then destained to visualize the nematodes, which were stained red. The roots were then observed under a microscope for detection of GUS expression.

For each transgenic line, 10 randomly picked syncytia were observed and scored for intensity of GUS expression at 12 Days after infection (DAI). The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "+" for weak staining, "++" for strong staining. The results for lines transformed with pAW283, RAW448, and RAW437 are presented in FIG. 8.

The 1603 by promoter sequence contained in RAW448 did not demonstrate nematode-induced expression in syncytia. The 482 by promoter sequence contained in RAW437 did demonstrate nematode-induced expression in syncytia.

Example 8

PLACE Analysis of Promoters

PLACE (National Institute of Agrobiological Sciences, Ibaraki, Japan) analysis results indicate a TATA box localized at nucleotide position 1995 to nucleotide position 2001 of SEQ ID NO:1 as shown in FIG. 1. In consequence, the 5' untranslated region starts at about nucleotide position 2028. The sequence described by SEQ ID NO:1 ends immediately before the ATG start codon. The potential core region of the promoter described by SEQ ID NO:1 is from nucleotide position 1677 to nucleotide position 2027.

---

What is claimed is:

1. An expression cassette comprising:
   (i) an isolated promoter polynucleotide selected from the group consisting of:
      a) a polynucleotide comprising nucleotides 1 to 2085 of SEQ ID NO:1;
      b) a polynucleotide comprising nucleotides 1677 to 2027 of SEQ ID NO:1; and
      c) a polynucleotide comprising nucleotides 1604 to 2085 of SEQ ID NO: 1; and
   (ii) a second polynucleotide operably linked to the isolated promoter polynucleotide, wherein said second polynucleotide is other than an *Arabidopsis thaliana* peroxidase encoded at locus At5g05340.

2. The expression cassette of claim 1, wherein said second polynucleotide confers to a plant a trait or property selected from the group consisting of yield, increased resistance under stress conditions, increased nutritional quality, increased resistance to nematodes, increased resistance to fungal disease, and increased or modified protein or oil content of a plant.

3. The expression cassette of claim 1, wherein said second polynucleotide encodes an agent that disrupts metabolism, growth, and/or reproduction of a plant parasitic nematode, that confers or improves plant resistance to a plant parasitic nematode, or that is toxic to a plant parasitic nematode.

4. A transgenic plant transformed with an expression cassette, wherein the expression cassette comprises an isolated promoter polynucleotide capable of mediating root-preferred or nematode-inducible expression, said promoter polynucleotide being selected from the group consisting of:

a) a polynucleotide comprising nucleotides 1 to 2085 of SEQ ID NO:1;
b) a polynucleotide comprising nucleotides 1677 to 2027 of SEQ ID NO:1; and
c) a polynucleotide comprising nucleotides 1604 to 2085 of a polynucleotide having the sequence as set forth in SEQ ID NO:1.

5. The transgenic plant of claim 4, wherein the expression cassette further comprises a second polynucleotide operably linked to the promoter polynucleotide.

6. The plant of claim 4, wherein the plant is a monocot.

7. The plant of claim 4, wherein the plant is a dicot.

8. The plant of claim 4, wherein the plant is selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, eggplant, pepper, oilseed rape, canola, beet, cabbage, cauliflower, broccoli, lettuce, *Lotus* sp., *Medicago trunculata*, perennial grass, ryegrass, and *Arabidopsis thaliana*.

9. The plant of claim 4, wherein the promoter polynucleotide comprises nucleotides 1 to 2085 of SEQ ID NO:1.

10. The plant of claim 4, wherein the promoter polynucleotide comprises nucleotides 1677 to 2027 of SEQ ID NO:1 or nucleotides 1604 to 2085 of SEQ ID NO:1.

* * * * *

SEQUENCE LISTING

```
<160> NUMBER OF SEQ ID NOS: 7

<210> SEQ ID NO 1
<211> LENGTH: 2085
<212> TYPE: DNA
<213> ORGANISM: Arabidopsis thaliana
<220> FEATURE:
<221> NAME/KEY: promoter
<222> LOCATION: (1)..(2027)
<220> FEATURE:
<221> NAME/KEY: misc_feature
<222> LOCATION: (1677)..(2027)
<223> OTHER INFORMATION: potential core region of promoter
<220> FEATURE:
<221> NAME/KEY: TATA_signal
<222> LOCATION: (1995)..(2001)
<220> FEATURE:
<221> NAME/KEY: 5'UTR
<222> LOCATION: (2028)..(2085)

<400> SEQUENCE: 1
cgaagagcat aagttttgtt caaatggccc aataacaaat taaaaacatg taaagtagtc      60
agtttaaaca agcatttgca taaagtgtgg ttaatattat attaaacttc acatccaatg     120
agcattcatg taatttaaag taactgaagt taagtatcta gaagcctttt tcttctattg     180
gttattaatt tgcttaattt tctttataag ttaatttctg gttggtgtga aaatgtgacc     240
ggagaaggta tctaactttt ttttttcttt aatgaattcc actaaaattt aattctgtat     300
gtaacgcata tagtaaaatc tagaaagcga ccggcgtgcc tcctttggaa agtaatcctg     360
taaaagtaaa agccgcgtag tgtaaaagta tatgacttct tcttcccata attattttat     420
aattagtctt taatctaaat atttaaacat ataattcgtt ttacgagaaa gatcttcaca     480
ctcgattagt atacattaca tttaattccc tagttcataa aatggataac aaaaggctgt     540
gcgagattac aactgtactt gataattttg tataaatata tcctttatga atatatttta     600
gcattgatga ccgtacatgg ttaatccagt ctgcagcata acggagtatg atattaaatg     660
aacactttct gttcgtatca aatggtatcg aatattatta gagtgatcat tcagaagaaa     720
aaaagagaga gaagaaaacc tacagtgtaa acatttttttt ttttgctaaa tacctacagt     780
gtaaacatga agtgctataa tttctgcaaa tagaaatcaa gaacagaaag agttgcttgg     840
aggaaaagaa atagaaaatt aagaaatcta gtgatgtaat aaatctttcc ataaaatcaa     900
atgtttggtc caaagtatta gttaaataat taggccacta ttcttgacaa ctcttttaa      960 caaactcttc tatattttct cgtggtacat atgctgaaaa agatgtatgt ctaatccata    1020
atatatctgt ataatgcgac tttcattatc tattagtacg acttctaacc tagaagataa    1080
caagcattag ctagggcatc aaaatcaacg tggaaaaacc tacgaaaagc acgaagtgat    1140
taatctgtgt aggggtggcg taagggtaaa gactaaagac tgagaatcta gggttcaagg    1200
cgtaaacttg ttctgctttt tgggtttcat tttattggcg aacaacattg atgtgtgtgg    1260
accatttggt gttcagggat tgagacaaga taatatgttt gctctcacct tctaggatta    1320
ctcgggtgct aagactcact tagtactatt gctatatcga tatactagtt cattaccaaa    1380
```

-continued

```
aaatggagtc ttcaaatttc gagttccaat atctgaaagc attgtttaaa gagatttgtt    1440
ttctccctgc acaattagtt tataacttca tatatacaca atcttatcaa tttacaacca    1500
ggtgtgtgtg aaccttcaca taatctctct tattcattca tgtatatatc caataaaagt    1560
tcgatatgtg aaattatata tctccatcta atgttagact attcccgggt cttgactata    1620
aatttaaagt attagacgag ctaattatat ttagcacaaa caatttcttc tgtaacagtg    1680
tcacgcttat cactaccaaa gaataaacac tgatctgttt taatctctta ttttctcacc    1740
catattcaaa gtcaactatt gcaagacttc gagataatta atttgatggc tatactattt    1800
acttgacatt tgggaaaata tattttcgct gataaatttg gtttttactt ctctctccga    1860
cggatataga aacaattcaa ttacatgcga aaatgataat tcaaccctat aaaccaaaac    1920
aaataacaga atgcacattt ttttcaacgc gttaggtcac ctatctttca ctttagaaca    1980
tcccttcacg tctctatata aacctcgact ctgttatcct ttgttcttca agtacaacaa    2040
tcaactctaa gtctattata ttcaagtctt tgttttaacc taaca                    2085

<210> SEQ ID NO 2
<211> LENGTH: 1301
<212> TYPE: DNA
<213> ORGANISM: Glycine max
<220> FEATURE:
<221> NAME/KEY: CDS
<222> LOCATION: (49)..(1011)

<400> SEQUENCE: 2
agcaaacaca aacacttgaa gtactaagtt agtgttttg agcaaaact atg gct tcg      57
                                                    Met Ala Ser
                                                      1 ttt tgt tct aga ttg acc att tgt ttg gct ctg ttt gtc ctc ata ttg     105
Phe Cys Ser Arg Leu Thr Ile Cys Leu Ala Leu Phe Val Leu Ile Leu
  5                  10                  15 ggg agt gcc aat gcc caa ctt tct aca aac ttc tac tac cat tcg tgt     153
Gly Ser Ala Asn Ala Gln Leu Ser Thr Asn Phe Tyr Tyr His Ser Cys
 20                  25                  30                  35 cca aac ctc ttc tcc act gtg aaa tcc aca gtg caa tct gcc ata tca     201
Pro Asn Leu Phe Ser Thr Val Lys Ser Thr Val Gln Ser Ala Ile Ser
                 40                  45                  50 aag gag acc cgc atg ggt gct tct ctc ctc cgc ctg ttc ttc cac gat     249
Lys Glu Thr Arg Met Gly Ala Ser Leu Leu Arg Leu Phe Phe His Asp
             55                  60                  65 tgc ttt gtc aat gga tgt gat ggt tca att cta ttg gat gac aca tca     297
Cys Phe Val Asn Gly Cys Asp Gly Ser Ile Leu Leu Asp Asp Thr Ser
         70                  75                  80 agc ttc acc gga gag aag aac gca aac ccc aac agg aac tct gct cgt     345
Ser Phe Thr Gly Glu Lys Asn Ala Asn Pro Asn Arg Asn Ser Ala Arg
 85                  90                  95 gga tac gag gtc att gac aac att aaa tca gcc gtg gag aaa gca tgt     393
Gly Tyr Glu Val Ile Asp Asn Ile Lys Ser Ala Val Glu Lys Ala Cys
100                 105                 110                 115 cca gga gtt gtc tcc tgc gca gat atc ctt gcc ata gct gcc aga gac     441
Pro Gly Val Val Ser Cys Ala Asp Ile Leu Ala Ile Ala Ala Arg Asp
                120                 125                 130 tct gtt cag atc ctt gga ggc cct agt tgg aat gtt aaa gtt gga aga     489
Ser Val Gln Ile Leu Gly Gly Pro Ser Trp Asn Val Lys Val Gly Arg
            135                 140                 145 aga gac gct aga act gct agc caa tct gct gct aac aat ggc atc cct     537
Arg Asp Ala Arg Thr Ala Ser Gln Ser Ala Ala Asn Asn Gly Ile Pro
        150                 155                 160 cca ccc act tca aac ctt aac caa ctc atc tca aga ttc agc gct ctt     585
```

```
                Pro Pro Thr Ser Asn Leu Asn Gln Leu Ile Ser Arg Phe Ser Ala Leu
                    165                 170                 175 gga ctt tcc acc aag gac ttg gtc gcc ttg tcc ggt ggt cac aca att              633
Gly Leu Ser Thr Lys Asp Leu Val Ala Leu Ser Gly Gly His Thr Ile
180                 185                 190                 195 gga caa gca agg tgc aca aac ttc aga gcc cgc atc tac aac gag agc              681
Gly Gln Ala Arg Cys Thr Asn Phe Arg Ala Arg Ile Tyr Asn Glu Ser
                200                 205                 210 aac ata gac acc gca ttt gca agg aca agg caa caa agc tgc cca aga              729
Asn Ile Asp Thr Ala Phe Ala Arg Thr Arg Gln Gln Ser Cys Pro Arg
            215                 220                 225 aca tca ggg tca ggg gac aat aat ctt gca acg ctt gat ctt caa act              777
Thr Ser Gly Ser Gly Asp Asn Asn Leu Ala Thr Leu Asp Leu Gln Thr
        230                 235                 240 cca acc gaa ttc gac aac tac tac ttc aag aat ctt gtt cag aag aag              825
Pro Thr Glu Phe Asp Asn Tyr Tyr Phe Lys Asn Leu Val Gln Lys Lys
    245                 250                 255 ggt ctc ctc cac tct gat cag caa ctg ttc aat ggt ggg tcc acc gac              873
Gly Leu Leu His Ser Asp Gln Gln Leu Phe Asn Gly Gly Ser Thr Asp
260                 265                 270                 275 tcc att gtg cgt ggc tac agc acc aac ccg agc tcc ttc tcc tct gac              921
Ser Ile Val Arg Gly Tyr Ser Thr Asn Pro Ser Ser Phe Ser Ser Asp
                280                 285                 290 ttc gcc gcc gcc atg atc aag atg gga gac att agt cct ctc act ggc              969
Phe Ala Ala Ala Met Ile Lys Met Gly Asp Ile Ser Pro Leu Thr Gly
            295                 300                 305 tcc aac gga gaa atc agg aag aat tgt aga agg att aac taa                     1011
Ser Asn Gly Glu Ile Arg Lys Asn Cys Arg Arg Ile Asn
        310                 315                 320 ttactaattg agtctccaat attaagggtc ctactacaca tacgcaagca atttaattgt           1071
gtttaataag ttgttaaaac atgttttggt tgtgttttgg attccgtggt gggttaattt           1131
cctagtgtag ttgctgttat caatgccgta tacgttagtg tgtgttctac ttcccttttat          1191 ttttgtctct tttttacttt tccttgacta tattgtagga aaaaaaatcc tttatcaaga           1251
atttatcaag aacagagttt gcttttttga gaccgacacg cagcggccgc                      1301

<210> SEQ ID NO 3
<211> LENGTH: 320
<212> TYPE: PRT
<213> ORGANISM: Glycine max

<400> SEQUENCE: 3

Met Ala Ser Phe Cys Ser Arg Leu Thr Ile Cys Leu Ala Leu Phe Val
1               5                   10                  15

Leu Ile Leu Gly Ser Ala Asn Ala Gln Leu Ser Thr Asn Phe Tyr Tyr
            20                  25                  30

His Ser Cys Pro Asn Leu Phe Ser Thr Val Lys Ser Thr Val Gln Ser
        35                  40                  45

Ala Ile Ser Lys Glu Thr Arg Met Gly Ala Ser Leu Leu Arg Leu Phe
    50                  55                  60

Phe His Asp Cys Phe Val Asn Gly Cys Asp Gly Ser Ile Leu Leu Asp
65                  70                  75                  80

Asp Thr Ser Ser Phe Thr Gly Glu Lys Asn Ala Asn Pro Asn Arg Asn
                85                  90                  95

Ser Ala Arg Gly Tyr Glu Val Ile Asp Asn Ile Lys Ser Ala Val Glu
            100                 105                 110

Lys Ala Cys Pro Gly Val Val Ser Cys Ala Asp Ile Leu Ala Ile Ala
        115                 120                 125
```

Ala Arg Asp Ser Val Gln Ile Leu Gly Gly Pro Ser Trp Asn Val Lys
130                 135                 140

Val Gly Arg Arg Asp Ala Arg Thr Ala Ser Gln Ser Ala Ala Asn Asn
145                 150                 155                 160

Gly Ile Pro Pro Thr Ser Asn Leu Asn Gln Leu Ile Ser Arg Phe
            165                 170                 175

Ser Ala Leu Gly Leu Ser Thr Lys Asp Leu Val Ala Leu Ser Gly Gly
            180                 185                 190

His Thr Ile Gly Gln Ala Arg Cys Thr Asn Phe Arg Ala Arg Ile Tyr
            195                 200                 205

Asn Glu Ser Asn Ile Asp Thr Ala Phe Ala Arg Thr Arg Gln Gln Ser
210                 215                 220

Cys Pro Arg Thr Ser Gly Ser Gly Asp Asn Leu Ala Thr Leu Asp
225                 230                 235                 240

Leu Gln Thr Pro Thr Glu Phe Asp Asn Tyr Tyr Phe Lys Asn Leu Val
            245                 250                 255

Gln Lys Lys Gly Leu Leu His Ser Asp Gln Gln Leu Phe Asn Gly Gly
            260                 265                 270

Ser Thr Asp Ser Ile Val Arg Gly Tyr Ser Thr Asn Pro Ser Ser Phe
            275                 280                 285

Ser Ser Asp Phe Ala Ala Ala Met Ile Lys Met Gly Asp Ile Ser Pro
290                 295                 300

Leu Thr Gly Ser Asn Gly Glu Ile Arg Lys Asn Cys Arg Arg Ile Asn
305                 310                 315                 320

<210> SEQ ID NO 4
<211> LENGTH: 324
<212> TYPE: PRT
<213> ORGANISM: Arabidopsis thaliana

<400> SEQUENCE: 4

Met Ala Ser Asn Lys Leu Ile Ser Ile Leu Val Leu Val Val Thr Leu
1               5                   10                  15

Leu Leu Gln Gly Asp Asn Asn Tyr Val Val Glu Ala Gln Leu Thr Thr
            20                  25                  30

Asn Phe Tyr Ser Thr Ser Cys Pro Asn Leu Leu Ser Thr Val Gln Thr
            35                  40                  45

Ala Val Lys Ser Ala Val Asn Ser Glu Ala Arg Met Gly Ala Ser Ile
50                  55                  60

Leu Arg Leu Phe Phe His Asp Cys Phe Val Asn Gly Cys Asp Gly Ser
65                  70                  75                  80

Ile Leu Leu Asp Asp Thr Ser Ser Phe Thr Gly Glu Gln Asn Ala Ala
                85                  90                  95

Pro Asn Arg Asn Ser Ala Arg Gly Phe Asn Val Ile Asp Asn Ile Lys
            100                 105                 110

Ser Ala Val Glu Lys Ala Cys Pro Gly Val Val Ser Cys Ala Asp Ile
            115                 120                 125

Leu Ala Ile Ala Ala Arg Asp Ser Val Val Ala Leu Gly Gly Pro Asn
            130                 135                 140

Trp Asn Val Lys Val Gly Arg Arg Asp Ala Arg Thr Ala Ser Gln Ala
145                 150                 155                 160

Ala Ala Asn Ser Asn Ile Pro Ala Pro Thr Ser Ser Leu Ser Gln Leu
            165                 170                 175

Ile Ser Ser Phe Ser Ala Val Gly Leu Ser Thr Arg Asp Met Val Ala
            180                 185                 190

```
Leu Ser Gly Ala His Thr Ile Gly Gln Ser Arg Cys Thr Asn Phe Arg
            195                 200                 205

Ala Arg Ile Tyr Asn Glu Thr Asn Ile Asn Ala Ala Phe Ala Thr Thr
    210                 215                 220

Arg Gln Arg Thr Cys Pro Arg Ala Ser Gly Ser Gly Asp Gly Asn Leu
225                 230                 235                 240

Ala Pro Leu Asp Val Thr Thr Ala Ala Ser Phe Asp Asn Asn Tyr Phe
                245                 250                 255

Lys Asn Leu Met Thr Gln Arg Gly Leu Leu His Ser Asp Gln Val Leu
            260                 265                 270

Phe Asn Gly Gly Ser Thr Asp Ser Ile Val Arg Gly Tyr Ser Asn Asn
        275                 280                 285

Pro Ser Ser Phe Asn Ser Asp Phe Thr Ala Ala Met Ile Lys Met Gly
    290                 295                 300

Asp Ile Ser Pro Leu Thr Gly Ser Ser Gly Glu Ile Arg Lys Val Cys
305                 310                 315                 320

Gly Arg Thr Asn

<210> SEQ ID NO 5
<211> LENGTH: 27
<212> TYPE: DNA
<213> ORGANISM: unknown
<220> FEATURE:
<223> OTHER INFORMATION: forward primer for At5g05340
<220> FEATURE:
<221> NAME/KEY: misc_feature
<222> LOCATION: (1)..(27)
<223> OTHER INFORMATION: forward primer for At5g05340

<400> SEQUENCE: 5
cccgggcgaa gagcataagt tttgttc                                       27

<210> SEQ ID NO 6
<211> LENGTH: 31
<212> TYPE: DNA
<213> ORGANISM: unknown
<220> FEATURE:
<223> OTHER INFORMATION: reverse primer for At5g05340
<220> FEATURE:
<221> NAME/KEY: misc_feature
<222> LOCATION: (1)..(31)
<223> OTHER INFORMATION: reverse primer for At5g05340

<400> SEQUENCE: 6
ggcgcgcctg ttaggttaaa acaaagactt g                                  31

<210> SEQ ID NO 7
<211> LENGTH: 324
<212> TYPE: PRT
<213> ORGANISM: Artificial Sequence
<220> FEATURE:
<223> OTHER INFORMATION: consensus amino acid sequence between
      arabidopsis and soybean sequences
<220> FEATURE:
<221> NAME/KEY: misc_feature
<222> LOCATION: (4)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
```

```
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (21)..(22)
<223> OTHER INFORMATION: Xaa can be any naturally occurring amino acid
<220> FEATURE:
<221> NAME/KEY: misc_feature
<222> LOCATION: (24)..(27)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (55)..(56)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (138)..(139)
<223> OTHER INFORMATION: Xaa can be any naturally occurring amino acid
<220> FEATURE:
<221> NAME/KEY: misc_feature
<222> LOCATION: (144)..(144)
<223> OTHER INFORMATION: Xaa can be any naturally occurring amino acid
<220> FEATURE:
<221> NAME/KEY: misc_feature
<222> LOCATION: (164)..(165)
<223> OTHER INFORMATION: Xaa can be any naturally occurring amino acid
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (174)..(174)
<223> OTHER INFORMATION: Xaa can be any naturally occurring amino acid
<220> FEATURE:
```

```
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (218)..(219)
<223> OTHER INFORMATION: Xaa can be any naturally occurring amino acid
<220> FEATURE:
<221> NAME/KEY: misc_feature
<222> LOCATION: (223)..(223)
<223> OTHER INFORMATION: Xaa can be any naturally occurring amino acid
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (232)..(232)
<223> OTHER INFORMATION: Xaa can be any naturally occurring amino acid
<220> FEATURE:
<221> NAME/KEY: misc_feature
<222> LOCATION: (238)..(238)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (248)..(250)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (261)..(262)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (287)..(287)
<223> OTHER INFORMATION: Xaa can be any naturally occurring amino acid
<220> FEATURE:
<221> NAME/KEY: misc_feature
<222> LOCATION: (293)..(293)
<223> OTHER INFORMATION: Xaa can be any naturally occurring amino acid
<220> FEATURE:
<221> NAME/KEY: misc_feature
<222> LOCATION: (297)..(297)
<223> OTHER INFORMATION: Xaa can be any naturally occurring amino acid
<220> FEATURE:
<221> NAME/KEY: misc_feature
<222> LOCATION: (313)..(313)
<223> OTHER INFORMATION: Xaa can be any naturally occurring amino acid
<220> FEATURE:
<221> NAME/KEY: misc_feature
<222> LOCATION: (319)..(319)
<223> OTHER INFORMATION: Xaa can be any naturally occurring amino acid
<220> FEATURE:
<221> NAME/KEY: misc_feature
<222> LOCATION: (321)..(321)
<223> OTHER INFORMATION: Xaa can be any naturally occurring amino acid
<220> FEATURE:
<221> NAME/KEY: misc_feature
<222> LOCATION: (323)..(323)
<223> OTHER INFORMATION: Xaa can be any naturally occurring amino acid

<400> SEQUENCE: 7

Met Ala Ser Xaa Xaa Xaa Xaa Xaa Xaa Ile Xaa Leu Xaa Leu Xaa Leu
1               5                   10                  15
```

```
Leu Ile Xaa Gly Xaa Xaa Asn Xaa Xaa Xaa Xaa Ala Gln Leu Ser Thr
        20              25                      30

Asn Phe Tyr Xaa Xaa Ser Cys Pro Asn Leu Xaa Ser Thr Val Xaa Ser
            35              40              45

Xaa Val Xaa Ser Ala Ile Xaa Xaa Glu Xaa Arg Met Gly Ala Ser Ile
    50              55                  60

Leu Arg Leu Phe Phe His Asp Cys Phe Val Asn Gly Cys Asp Gly Ser
65              70                  75                      80

Ile Leu Leu Asp Asp Thr Ser Ser Phe Thr Gly Glu Xaa Asn Ala Xaa
            85                  90              95

Pro Asn Arg Asn Ser Ala Arg Gly Phe Xaa Val Ile Asp Asn Ile Lys
            100                 105             110

Ser Ala Val Glu Lys Ala Cys Pro Gly Val Val Ser Cys Ala Asp Ile
            115             120                 125

Leu Ala Ile Ala Ala Arg Asp Ser Val Xaa Xaa Leu Gly Gly Pro Xaa
    130             135                 140

Trp Asn Val Lys Val Gly Arg Arg Asp Ala Arg Thr Ala Ser Gln Ala
145             150                 155             160

Ala Ala Asn Xaa Xaa Ile Pro Xaa Pro Thr Ser Xaa Leu Xaa Gln Leu
            165             170             175

Ile Ser Xaa Phe Ser Ala Leu Gly Leu Ser Thr Lys Asp Leu Val Ala
        180                 185             190

Leu Ser Gly Ala His Thr Ile Gly Gln Ala Arg Cys Thr Asn Phe Arg
        195             200             205

Ala Arg Ile Tyr Asn Glu Ser Asn Ile Xaa Xaa Ala Phe Ala Xaa Thr
    210             215             220

Arg Gln Xaa Ser Cys Pro Arg Xaa Ser Gly Ser Gly Asp Xaa Asn Leu
225         230             235                     240

Ala Xaa Leu Asp Leu Xaa Thr Xaa Xaa Xaa Phe Asp Asn Xaa Tyr Phe
        245             250                     255

Lys Asn Leu Met Xaa Xaa Lys Gly Leu Leu His Ser Asp Gln Xaa Leu
            260             265                 270

Phe Asn Gly Gly Ser Thr Asp Ser Ile Val Arg Gly Tyr Ser Xaa Asn
        275             280                 285

Pro Ser Ser Phe Xaa Ser Asp Phe Xaa Ala Ala Met Ile Lys Met Gly
        290             295                 300

Asp Ile Ser Pro Leu Thr Gly Ser Xaa Gly Glu Ile Arg Lys Xaa Cys
305             310             315                     320

Xaa Arg Xaa Asn
```